(12) United States Patent
Schwartz et al.

(10) Patent No.: US 6,339,173 B1
(45) Date of Patent: *Jan. 15, 2002

(54) AMIDE-BASED CATIONIC LIPIDS

(75) Inventors: David Aaron Schwartz, Encinitas; William J. Daily, Atascadero; Brian Patrick Dwyer; Kumar Srinivasan, both of San Diego; Bob Dale Brown, Encinitas, all of CA (US)

(73) Assignee: Promega Biosciences, Inc., Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/327,392

(22) Filed: Jun. 7, 1999

Related U.S. Application Data

(63) Continuation of application No. 08/681,297, filed on Jul. 22, 1996, now Pat. No. 6,020,526.

(51) Int. Cl.[7] .............................................. C07C 233/05
(52) U.S. Cl. ........................ 564/153; 554/35; 554/36; 554/51; 554/52; 562/561; 562/563; 564/159; 564/197
(58) Field of Search ................................ 564/153, 159, 564/197; 562/561, 563; 554/35, 36, 51, 52

(56) References Cited

U.S. PATENT DOCUMENTS

| | | |
|---|---|---|
| 4,897,355 A | 1/1990 | Eppstein et al. |
| 5,171,678 A | 12/1992 | Beher et al. |
| 5,264,618 A | 11/1993 | Felger et al. |
| 5,334,761 A | 8/1994 | Gebeyehu et al. |
| 5,650,096 A * | 7/1997 | Harris et al. ............... 252/357 |
| 5,747,471 A * | 5/1998 | Siegel et al. ................ 514/44 |
| 6,020,526 A * | 2/2000 | Schwartz et al. ........... 564/153 |

FOREIGN PATENT DOCUMENTS

WO 9601841 1/1996

OTHER PUBLICATIONS

Felgner et al., Lipofection: A highly efficient, lipid–mediated DNA–transfection procedure, Proc. Natl. Acad. Sci. USA, 84:7413–7417, 1978.

Remy et al., Bioconjugate chem, vol. 5, pp. 647–654, 1994.

* cited by examiner

Primary Examiner—Shailendra Kumar
(74) Attorney, Agent, or Firm—Michael Best & Friedrich LLP; Grady J. Frenchick

(57) ABSTRACT

The present invention provides novel amide-based cationic lipids of the general structure:

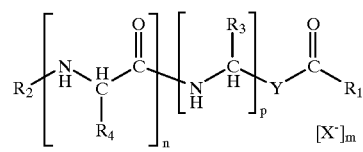

or a salt, or solvate, or enantiomers thereof wherein; (a) Y is a direct link or an alkylene of 1 to about 20 carbon atoms; (b) $R_1$ is H or a lipophilic moiety; (c) $R_2$, $R_3$, and $R_4$ are positively charged moieties, or at least one but not all of $R_2$, $R_3$, or $R_4$ is a positive moiety and the remaining are independently selected from H, an alkyl moiety of 1 to about 6 carbon atoms, or a heterocyclic moiety of about 5 to about 10 carbon atoms; (d) n and p are independently selected integers from 0 to 8, such that the sum of n and o is from 1 to 16; (e) $X^-$ is an anion or polyanion and (f) m is an integer from 0 to a number equivalent to the positive charge(s) present on the lipid; provided that if Y is a direct link and the sum of n and p is 1 then one of either $R_3$ or $R_4$ must have an alkyl moiety of at least 10 carbon atoms.

The present invention further provides compositions of these lipids with polyanionic macromolecules, methods for interfering with protein expression in a cell utilizing these compositions and a kit for preparing the same.

15 Claims, 6 Drawing Sheets

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (xi) SEQUENCE DESCRIPTION: SEQ ID NO: 1:

GCCUAUUUCC CUAUUUCCCU AAAGGGUUUA UUGAGAAUA          39

(2) INFORMATION FOR SEQ ID NO: 2:

(i) SEQUENCE CHARACTERISTICS:
         (A) LENGTH: 120 base pairs
         (B) TYPE: nucleic acid
         (C) STRANDEDNESS: single
         (D) TOPOLOGY: linear (xi) SEQUENCE DESCRIPTION: SEQ ID NO: 2:

ACCUGGCCUA UUUCCCUAAA GGUGAGUGAC UAACUAAGUC GACUGCAGAC UAGUCAUUGA          60

UUGAGUGUAA CAAGACCGGA UAUCUUCGAA CCUCUCUCUC UCUCUCAGGG UUUAUUGAGA          120

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 3:

GGTATATCCA GTGATCTTCT TCTC        24

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 4:

GGTATATCCA GTGATCTTCT TCTC        24

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 5:

GGUAUAUCCA GUGAUCUUCU T        21

AMIDE-BASED CATIONIC LIPIDS

This application is a continuation of 08/681,297, filed Jul. 22, 1996, now U.S. Pat. No. 6,020,526.

TECHNICAL FIELD

The present invention is directed to novel amide-based cationic lipid compounds useful in lipid aggregates for the delivery of macromolecules into cells.

BACKGROUND OF THE INVENTION

Lipid aggregates, such as liposomes, have been previously reported to be useful as agents for the delivery of macromolecules such as DNA, RNA, oligonucleotides, proteins, and pharmaceutical compounds into cells. In particular, lipid aggregates which include charged as well as uncharged lipids have been especially effective for delivering polyanionic molecules to cells. The reported effectiveness of cationic lipids may result from charge inmteractions with cells which are said to bear a net negative charge. It has also been postulated that the net positive charge on the cationic lipid aggregates may enable them to bind polyanions, such as nucleic acids. Lipid aggregates containing DNA have been reported to be effective agents for efficient transfection of cells.

The structure of various types of lipid aggregates vary depending on factors which include composition and methods of forming the aggregate. Lipid aggregates include, for example, liposomes, unilamellar vesicles, multilamellar vesicles, micelles and the like, and may have particle sizes in the nanometer to micrometer range. Various methods of making lipid aggregates have been reported in the art. One type of lipid aggregate comprises phospholipid containing liposomes. An important drawback to the use of this type of aggregate as a cell delivery vehicle is that the liposome has a negative charge that reduces the efficiency of binding to a negatively charged cell surface. It has been reported that positively charged liposomes that are able to bind DNA may be formed by combining cationic lipid compounds with phospholipids. These liposomes may then be utilized to transfer DNA into target cells. (See, e.g. Felgner et al., *Proc. Nat. Acad. Sci.* 84:7413–7417, 1987; Eppstein et al. U.S. Pat. No. 4,897,355; Feigner et al. U.S. Pat. No. 5,264,618; and Gebeyehu et al. U.S. Pat. No. 5,334,761).

Known cationic lipids include N[1-(2,3-dioleoyloxy) propyl]-N,N,N-trimethyl-ammonium chloride ("DOTMA") and combinations of DOTMA with dioleoylphosphatidyle-thanolamine ("DOPE") are commercially available. Formulation of DOTMA, either by itself or in 1:1 combination with DOPE, into liposomes by conventional techniques has been reported. However, compositions comprising DOTMA have been reported to show some toxicity to cells.

Another commercially available cationic lipid, 1,2-bis (oleoyloxy)-3,3-(trimethylammonia)propane ("DOTAP") differs from DOTMA in that the oleoyl moieties are linked by ester, rather than ether, linkages to the propylamine. However, DOTAP is reported to be more readily degraded by target cells. Other cationic lipids which represent structural modifications of DOTMA and DOTAP have also been reported.

Other reported cationic lipid compounds include those which have been conjugated to a variety of moieties including, for example, carboxyspermine which has been conjugated to one of two types of lipids and includes compounds such as 5-carboxyspermylglycine dioctaoleoy-lamide ("DOGS") and dipalmitoyl-phosphatidylethanolamine 5-carboxyspermyl-amide ("DPPES") (See, e.g. Behr et al., U.S. Pat. No. 5,171,678).

Another reported cationic lipid composition is a cationic cholesterol derivative ("DC-Chol") which has been formulated into liposomes in combination with DOPE. (See, Gao, X. and Huang, L., *Biochim. Biophys. Res. Commun.* 179:280, 1991). For certain cell lines, these liposomes were said to exhibit lower toxicity and provide more efficient transfection than the DOTMA-containing compositions.

Lipopolylysine, made by conjugating polylysine to DOPE has been reported to be effective for transfection in the presence of serum. (Zhou, X. et al., *Biochim. Biophys. Acta* 1065:8, 1991).

However, of the cationic lipids which have been proposed for use in delivering macromolecules to cells, no particular cationic lipid has been reported to work well with a wide variety of cell types. Since cell types differ from one another in membrane composition, different cationic lipid compositions and different types of lipid aggregates may be effective for different cell types, either due to their ability to contact and fuse with target cell membranes directly or due to different interactions with intracellular membranes or the intracellular environment. For these and other reasons, design of effective cationic lipids has largely been empirical. In addition, to content and transfer, other factors believed important include, for example, ability to form lipid aggregates suited to the intended purpose, toxicity of the composition to the target cell, stability as a carrier for the macromolecule to be delivered, and function in an in vivo environment. Thus, there remains a need for improved cationic lipids which are capable of delivering macromolecules to a wide variety cell types with greater effeciency.

SUMMARY OF THE INVENTION

In one aspect of the present invention novel amide-based cationic lipids having the structure:

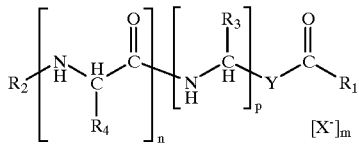

or a salt, or solvate, or enantiomers thereof are provided wherein; (a) Y is a direct link or an alkylene of 1 to about 20 carbon atoms; (b) $R_1$ is H or a lipophilic moiety; (c) $R_2$, $R_3$, and $R_4$ are positively charged moieties, or at least one but not all of $R_2$, $R_3$, or $R_4$ is a positively charged moiety and the remaining are independently selected from H, an alkyl moiety of 1 to about 6 carbon atoms or a heterocyclic moiety; (d) n and p are independently selected integers from 0 to 8, such that the sum of n and o is from 1 to 16; (e) $X^-$ is an anion or polyanion and (f) m is an integer from 0 to a number equivalent to the positive charge(s) present on the lipid; provided that if Y is a direct link and the sum of n and p is 1 then one of either $R_3$ or $R_4$ must have an alkyl moiety of at least 10 carbon atoms.

In one embodiment $R_1$ may be a variety of lipophilic moieties including a straight chain alkyl moiety of 1 to about 24 carbon atoms, a straight chain alkenyl moiety of 2 to about 24 carbon atoms, a symmetrical branched alkyl or alkenyl moiety of about 10 to about 50 carbon atoms, a unsymmetrical branched alkyl or alkenyl moiety of about 10 to about 50 carbon atoms, a steroidyl moiety, a amine derivative, a glyceryl derivative, or $OCH(R_5R_6)$ or $N(R_5R_6)$, wherein $R_5$ and R6 are straight chain or branched alkyl moieties of about 10 to about 30 carbon.

In another embodiment when $R_2$, $R_3$, or $R_4$ are positively charged moieties it is preferable that the positively charged moiety be an alkylamine moiety, a fluoroalkylamine moiety, or a perfluoroalkylamine moiety of 1 to about 6 carbon atoms, an arylamine moiety or an aralkylamine moiety of 5 to about 10 carbon atoms, a guanidinium moiety, an enamine moiety, a cyclic amine moiety, an amidine moiety, an isothiourea moiety, and a substituted heterocyclic amine moiety, a substituted heterocyclic moiety or a substituted alkyl moiety of 1 to about 6 carbon atoms substituted with a substituent selected from the group consisting of $NH_2$, $C(=O)NH_2$, $NHR_7$, $C(=O)NHR_7$, $NHR_7R_4$, or $C(=O)NHR_7R_8$, wherein $R_7$ and $R_8$ are independently selected from an alkyl moiety of 1 to about 24 carbon atoms, an alkenyl moiety of 2 to about 24 carbon atoms, an aryl moiety of about 5 to about 20 carbon atoms, and an aralkyl moiety of about 6 to about 25 carbon atoms.

When any of $R_2$, $R_3$, or $R_4$ are not a positively charged moiety it is preferable that the at least one but not all of $R_2$, $R_3$, or $R_4$ are independently selected from a substituted heterocyclic moiety of 1 to about 6 carbon atoms, or a substituted alkyl moiety of 1 to about 6 carbon atoms substituted with substituents selected from OH, thio, aryl of 1 to about 20 carbon atoms, or $OR_7$, wherein $R_7$ is an alkyl moiety of 1 to about 24 carbon atoms, an alkenyl of 2 to about 24 carbon atoms, an aryl of about 5 to about 20 carbon atoms or an aralkyl of about 6 to about 25 carbon atoms.

It is particularly prefered that when $R_2$, $R_3$, or $R_4$ is an arylamine moiety that it be tryptophane, phenylanaline, or tyrosine.

In another prefered embodiment $R_2$ is an amino acid residue having a positively charged side chain wherein the amino group(s) may be optionally substituted with an alkyl of 1 to about 6 carbon atoms or substituted to form a secondary, tertiary, or quaternary amine with an alkyl moiety of 1 to about 6 carbon atoms optionally substituted with substituents selected from hydroxyl, amino, alkoxy moiety of 1 to about 6 carbon atoms, alkylamino moiety of 1 to about 6 carbon atoms, or dialkylamino moiety of 2 to about 12 carbon atoms.

Preferably when $R_1$ is steroidyl moiety it is a cholesteryl moiety.

It is preferable when $R_2$ is an amino acid that it be lysine, arginine, histidine, ornithine, or an amino acid analog. In particular, when $R_2$ is an amino acid analog it is preferable that it be 3-carboxyspermidine, 5-carboxyspermidine, 6-carboxyspermine, or monoalkyl, dialkyl, or peralkyl substituted derivatives which are substituted on one or more amine nitrogens with an alkyl group of 1 to about 6 carbon atoms.

It is prefereable that $R_3$ and $R_4$ independently be a lipophilic moiety of 1 to about 24 carbon atoms, a positively charged moiety, or a negatively charged moiety. In particular, when both or either $R_3$ and $R_4$ are a lipohilic moiety it is preferable that it be a straight chain alkyl moiety of 1 to about 24 carbon atoms, a straight chain alkenyl moiety of 2 to about 24 carbon atoms, a symmetrical branched alkyl or alkenyl moiety of about 10 to about 50 carbon atoms, a unsymmetrical branched alkyl or alkenyl moiety of about 10 to about 50 carbon atoms, an aryl moiety of about 5 to about 20 carbon atoms, an aralkyl moiety of about 6 to about 25 carbon atoms, or a steroidyl moiety.

When both or either $R_3$ and $R_4$ are a positively charged moiety it is preferable that the moiety be an amino acid residue having a positively charged group on the side chain, an alkylaminoalkyl moiety, a fluoroalkylaminoalkyl moiety, a perfluoroalkylaminoalkyl moiety, a guanidiniumalkyl moiety, an enaminoalkyl moiety, a cyclic aminoalkyl moiety, an amidinoalkyl moiety, an isothiourea alkyl moiety, or a heterocyclic amine moiety.

It is also preferable that when both or either $R_3$ and $R_4$ are a negatively charged moiety it be a carboxyalkyl moiety, a phosphonoalkyl moiety, a sulfonoalkyl moiety, or a phosphatidylalkyl moiety of 1 to about 24 carbon atoms.

It is further prefered that the sum of the integers n and p be from 1 to 8, more preferably from 1 to 4 and most preferably from 1 to 2.

It is also preferable that $X^-$ be a pharmaceutically acceptable anion or polyanion.

In a particularly prefered embodiment the amide-based cationic lipid has the structure.

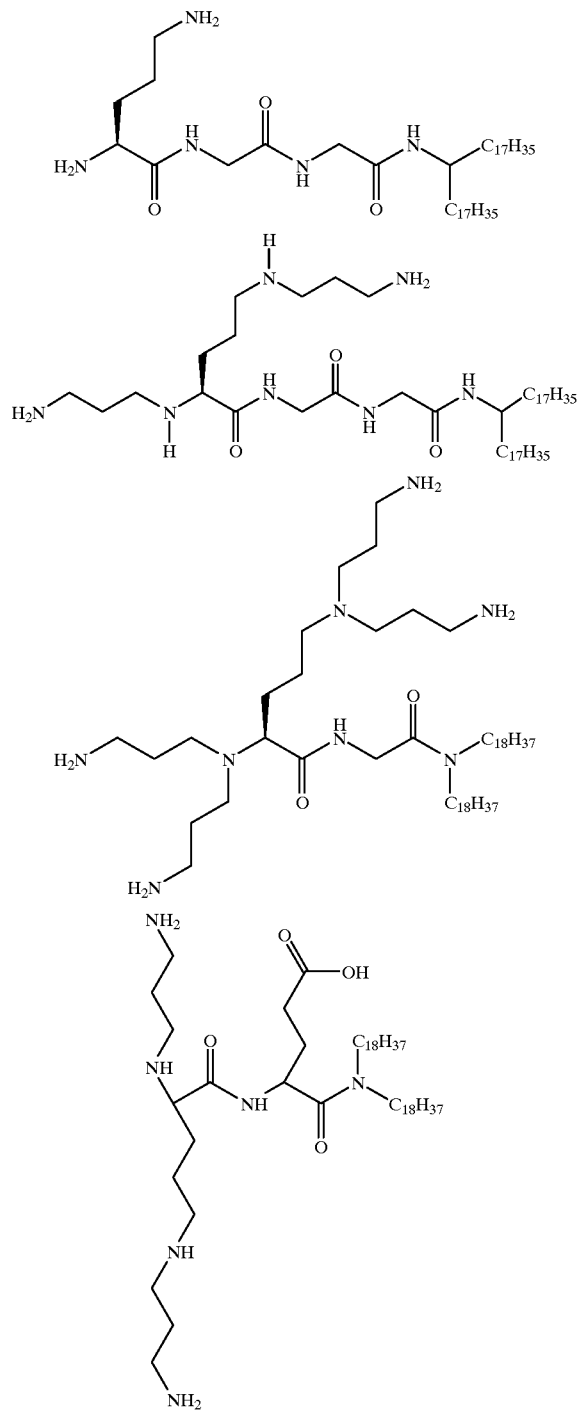

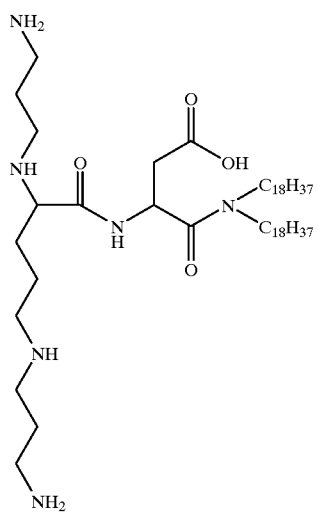
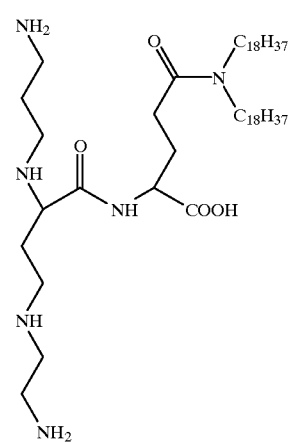
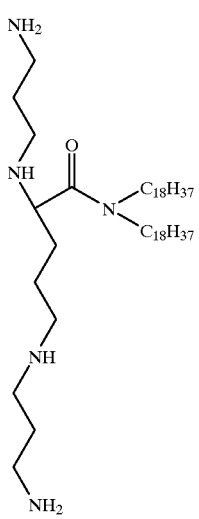
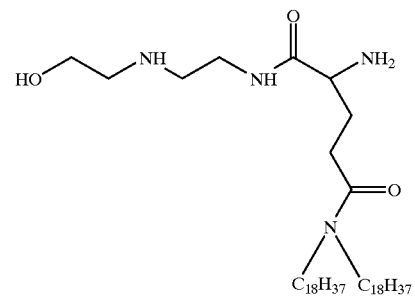
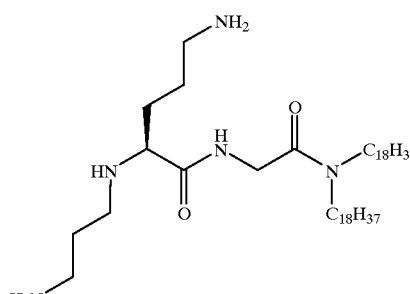
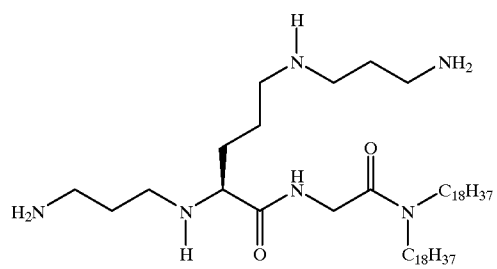
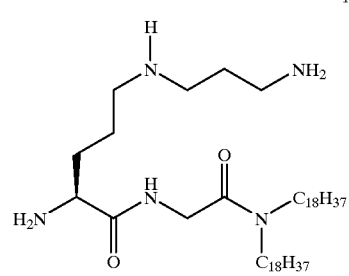
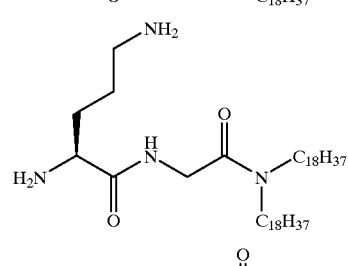
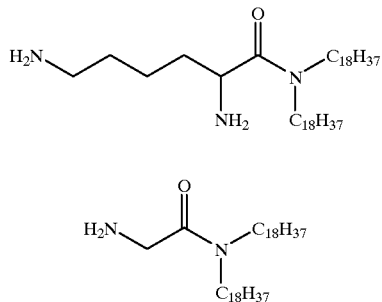

-continued

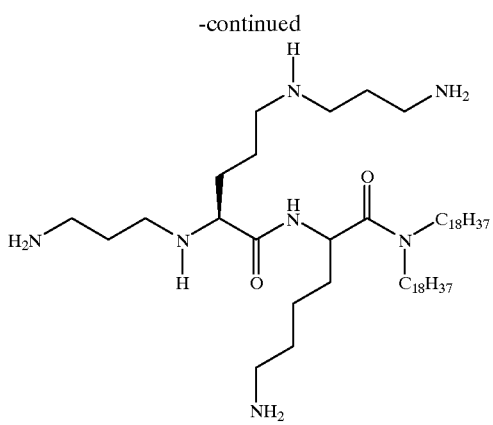

In another aspect of the present invention compositions comprising a polyanionic macromolecule and any of the lipids described above are provided. In particular, the polyanionic macromolecule may be a variety of molecules including an expression vector capable of expressing a polypeptide in a cell. In a prefered embodiment the polyanionic macromolecule is an oligomucleotide or an oligomer and most preferably DNA.

In still another aspect of the invention methods for the delivery of a polyanionic macromolecule into a cell by contacting any of the compositions above with the cell are provided. In particular, a method is provided to interfere with the expression of a protein in a cell by contacting any of the the compositions described above with a cell wherein the composition comprises an oligomer having a base sequence that is substantially complimentary to an RNA sequence in the cell that encodes the protein.

The present invention further provides a kit for delivering a polyanionic macromolecule into a cell comprising any of the compositions described above.

DETAILED DESCRIPTION OF THE INVENTION

Figure 1:
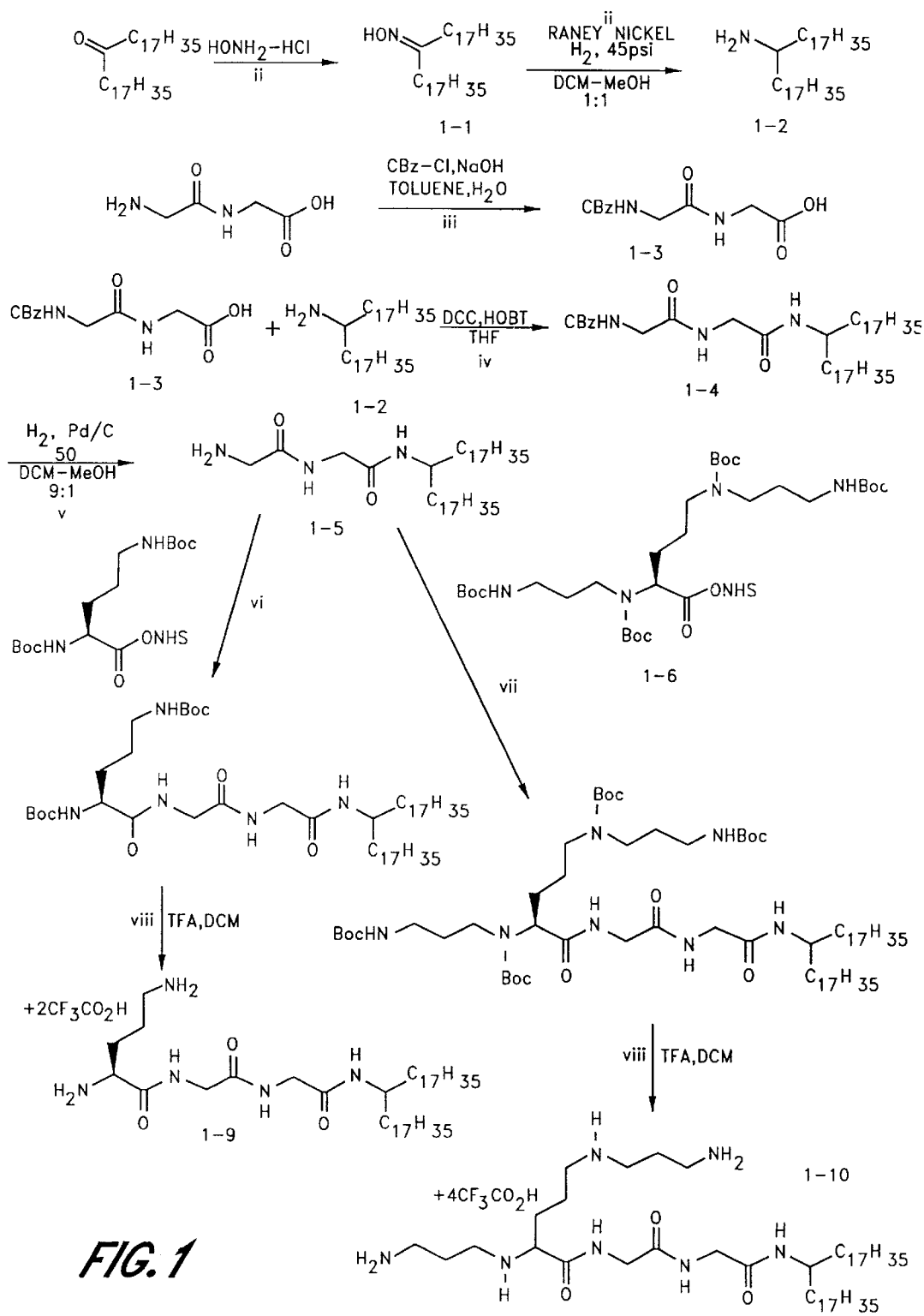
FIG. 1 depicts synthetic schemes for the preparation of compounds 1-9 and 1-10. In this figure, i denotes hydroxylamine hydrochloride; ii denotes Raney nickel, $H_2$ at 45 psi, and 1:1 dichloromethane:methanol; iii denotes benzyl chloroformate, aqueous sodium hydroxide, water and toluene; iv denotes dicyclohexylcarbodiimide ("DCC"), 1-hydroxybenzotriazole ("HOBT" or "HOBt") and tetrahydrofuran ("THF"); v denotes palladium on carbon, $H_2$ gas at 50 psi and 9:1 dichloromethane:methanol; vi denotes N,$N^2$-bis-[(1,1-dimethylethoxy)carbonyl]-L-ornithine, N-hydroxysuccinimidyl ester; vii denotes compound 1-6; and viii denotes trifluoroacetic acid and dichloromethane.
Figure 2:
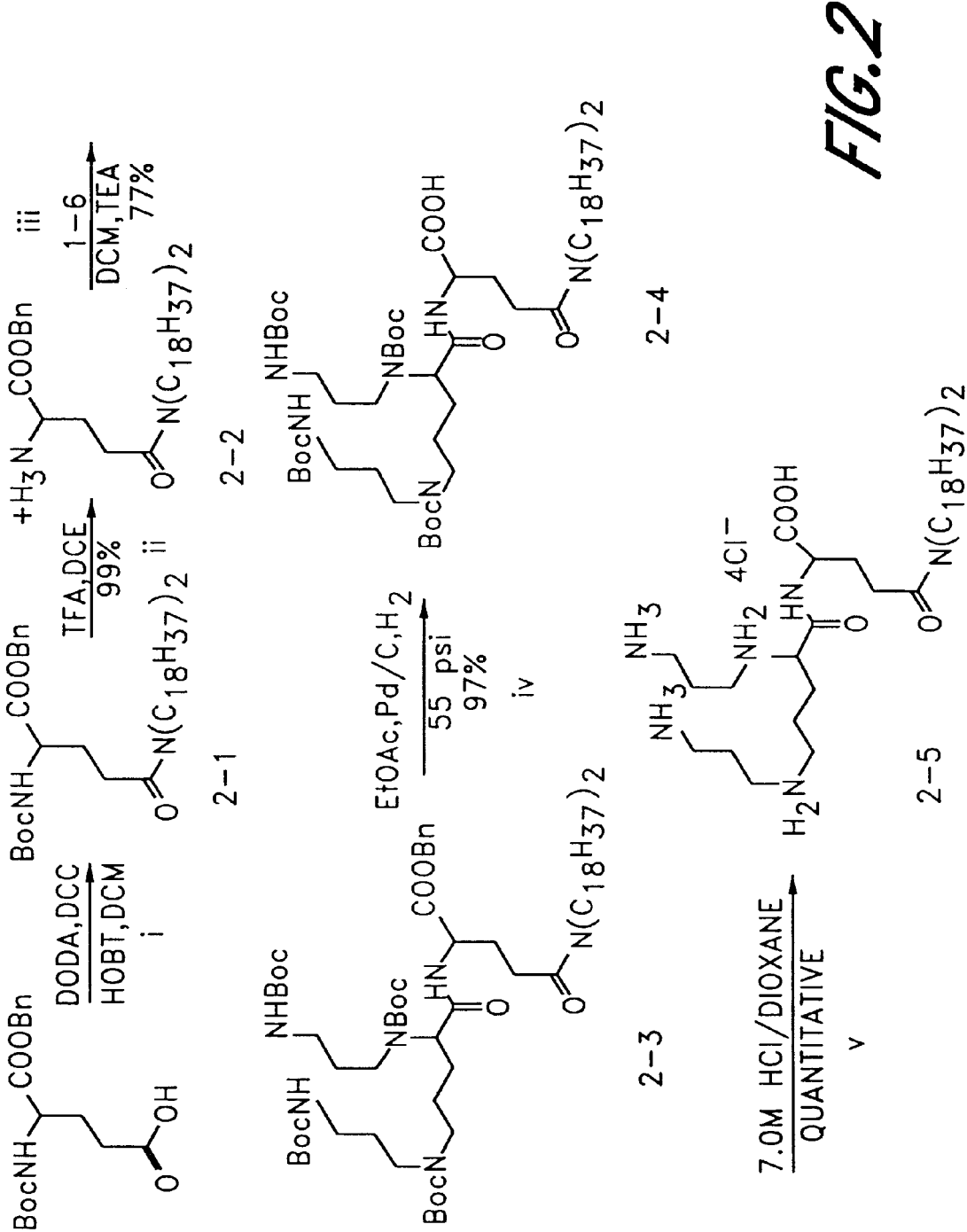
FIG. 2 depicts a synthetic scheme for the preparation of the compound 2-5. In this figure, i denotes dioctadecylamine ("DODA"), DCC, and HOBT in dichloromethane; ii denotes trifluoroacetic acid and 1,2-dichloroethane ("DCE") to give a quantitative (99%) yield of compound 2-2; iii denotes compound 1-6, $N^2,N^5$-bis[(1,1-dimethylethoxy)carbonyl]-$N^2,N^5$-bis[3-[(1,1-dimethylethoxy)carbonyl]amino-propyl]-L-ornithine, DCC and HOBT to give a 77% yield of compound 2-3; iv denotes 10% palladium on carbon and $H_2$ at 55 psi to give a 97% yield of compound 2-4; and v denotes 7.0 M HCl in dioxane to give a quantitative yield of compound 2-5.
Figure 3:
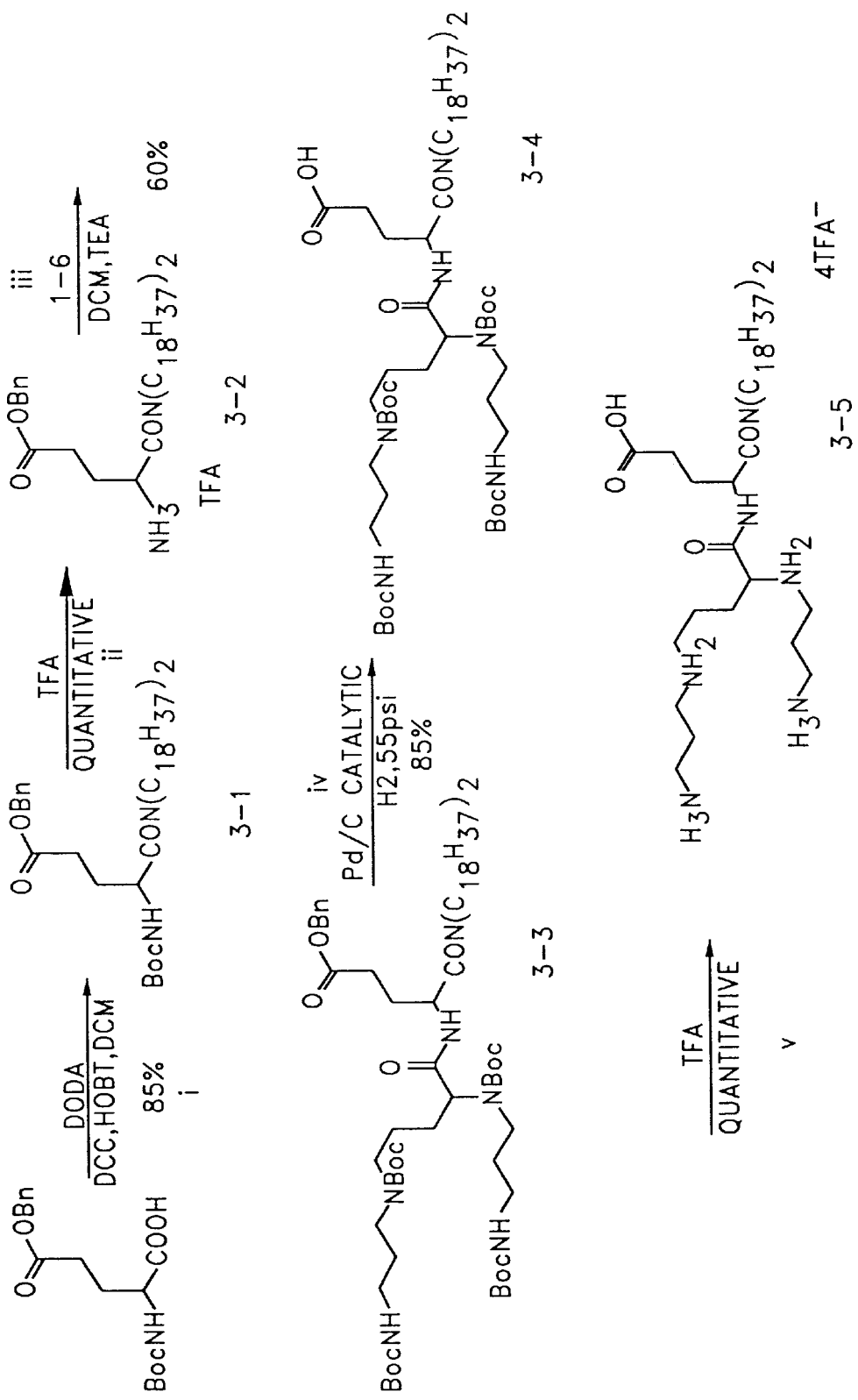
FIG. 3 depicts a synthetic scheme for the preparation of compound 3-5. In this figure, i denotes DODA, DCC and HOBT in dichloromethane to give a 85% yield of compound 3-1; ii denotes deprotection using 1:1 trifluoroacetic acid:dichloromethane to give a quantitative compound 3-2; iii denotes compound 1-6, triethylamine ("TEA") and DCM to give a 60% yield of compound 3-3; iv denotes catalytic hydrogenation using palladium on carbon and $H_2$ at 55 psi to give an 85% yield of compound 3-4; and v denotes Boc deprotection using 1:1 TFA:DCM to give a quantitative yield of compound 3-5.
Figure 4:
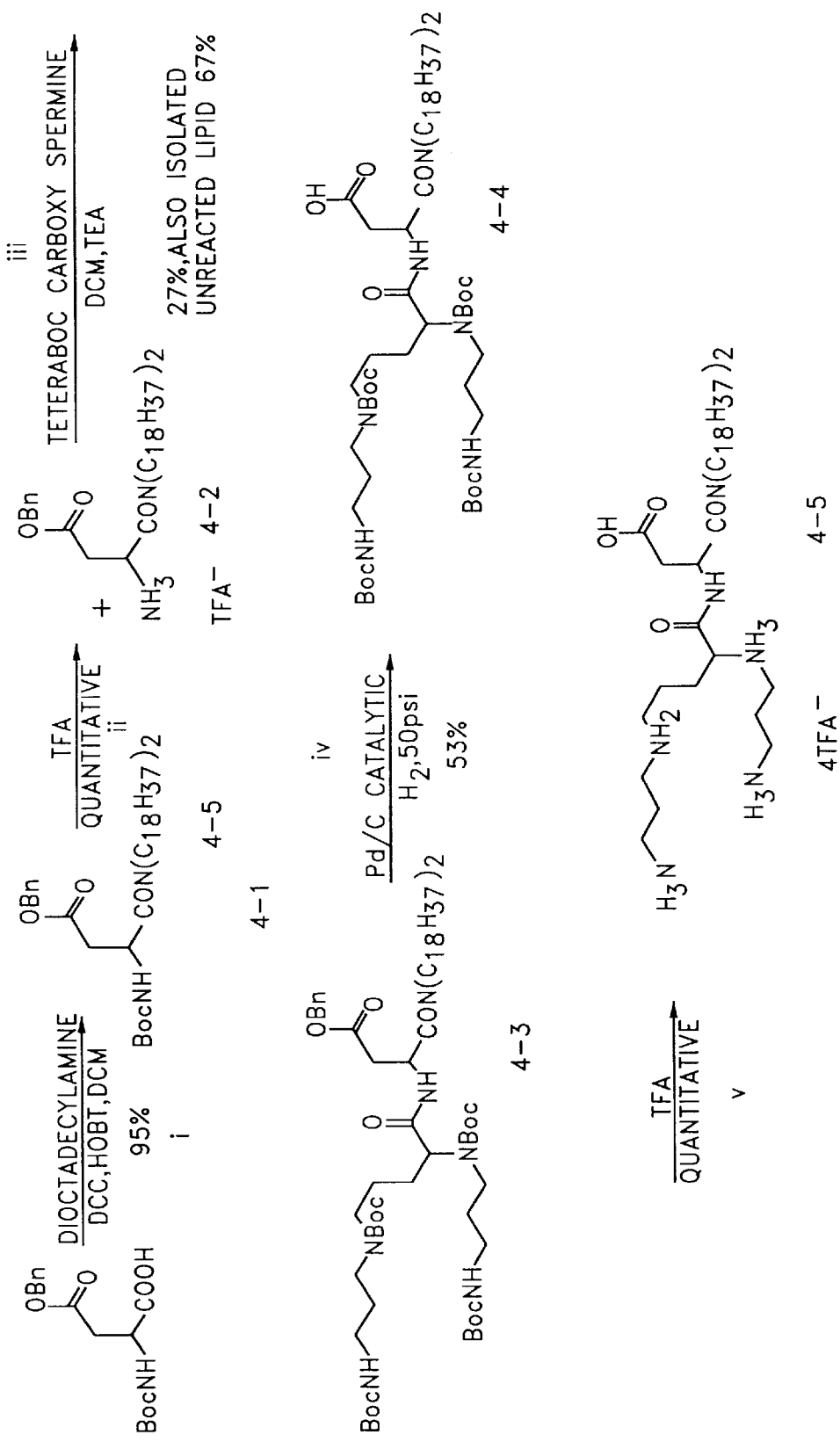
FIG. 4 depicts a reaction scheme for the preparation of compound 4-5. In this figure, i denotes DODA, DCC and HOBT in DCM to give a quantitative (95%) yield of compound 4-1; ii denotes TFA to give a quantitative yield of compound 4-2; iii denotes tetra-Boc-carboxy-spermidine, TEA and DCM to give a 27% yield of compound 4-3 (67% of unreacted lipid (compound 4-2) was isolated); iv denotes palladium on carbon and $H_2$ at 50 psi to give a 53% yield of compound 4-4; and v denotes Boc deprotection with TFA to give a 94% yield of compound 4-5.
Figure 5:
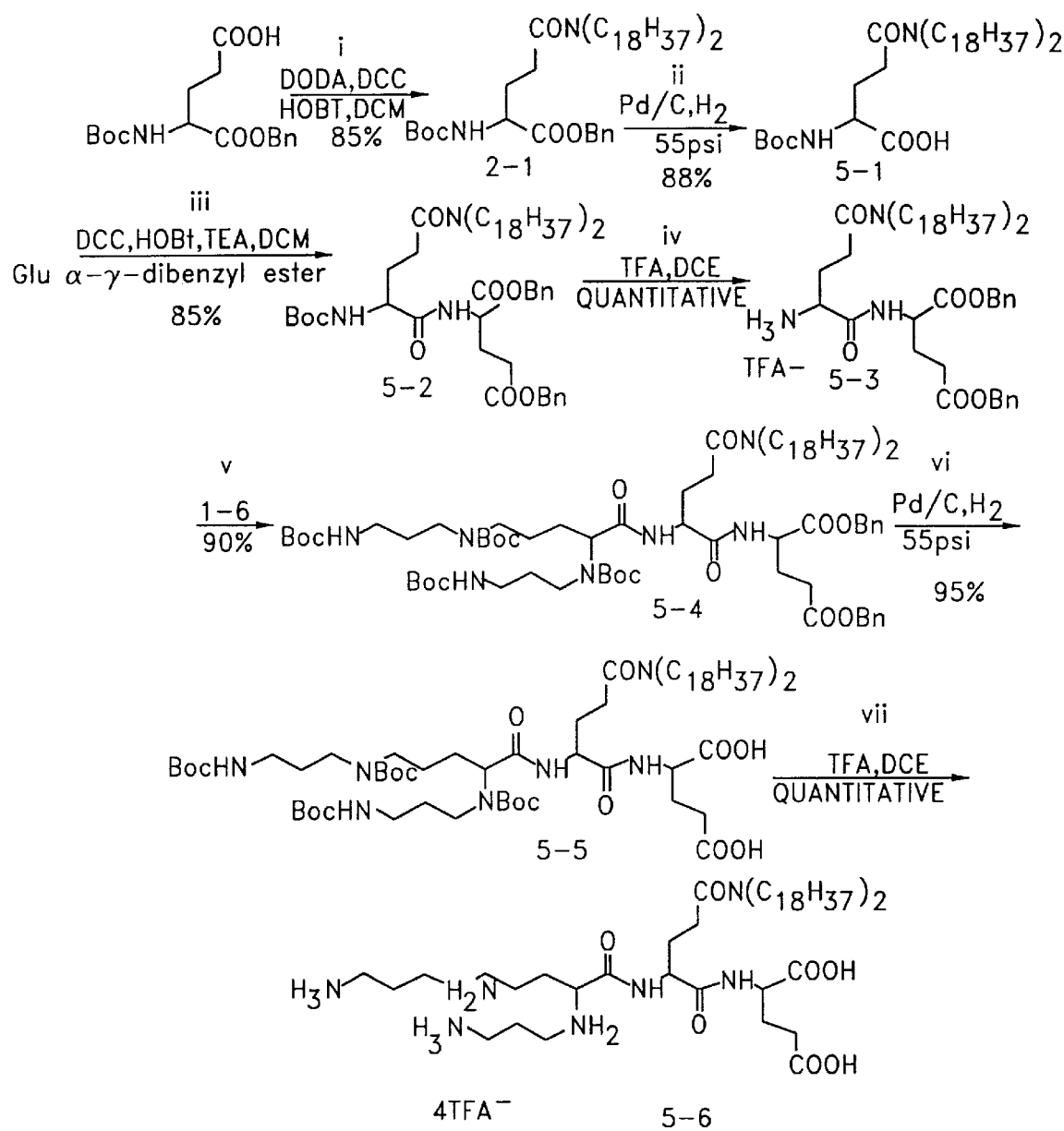
FIG. 5 depicts a reaction scheme for the preparation of compound 5-6. In this figure, i denotes DODA, DCC and HOBT in DCM to give an 85% yield of compound 2-1; ii denotes palladium on carbon with $H_2$ at 55 psi to give an 88% yield of compound 5-1; iii denotes L-glutamic acid bis(phenylamethyl)ester, toluene sulfonic acid salt, DCC, HOBT, TEA, and DCM to give a 85% yield of compound 5-2; iv denotes deprotection with TFA and DCE to give a quantitative yield of compound 5-3; v denotes compound 1-6 in DCM to give a 90% yield of compound 5-4; vi denotes palladium on carbon with $H_2$ at 55% psi to give 95% yield of compound 5-5; and vii denotes Boc deprotection with TFA and DCE to give a quantitative yield of compound 5-6.
Figure 6:
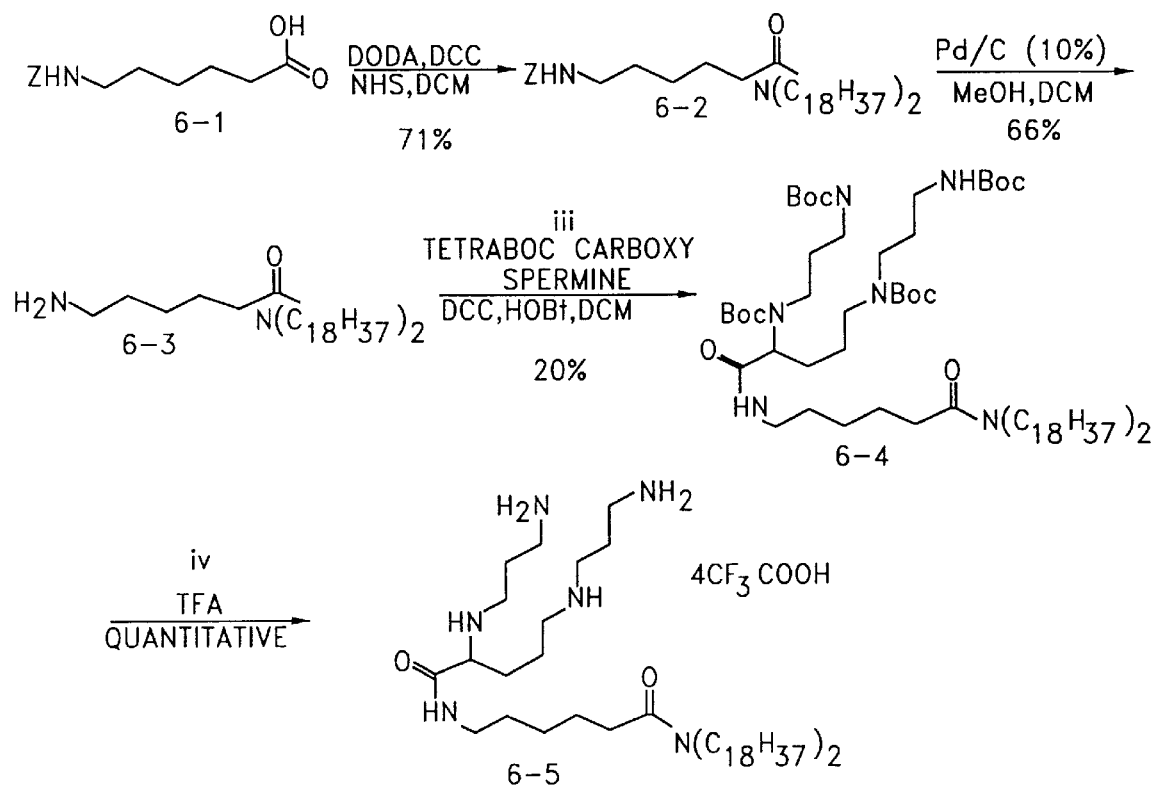
FIG. 6 depicts a reaction scheme for the preparation of compound 6-5. In this figure, i denotes DODA, DCC, and NHS in DCM to give n 70% yield of compound 6-2; ii denotes Pd/C in 2:1 methanol:DCM to give a 66% yield of compound 6-3; iii denotes TetraBoc carboxyspermine, DCC and HOBt in DCM to give a 20% yield of compound 6-4; and iv denotes TFA to give a quantitative yield of compound 6-5. In connection with compounds 6-1 and 6-2 "Z" represents benzyloxycarbonyl.
Figure 7:
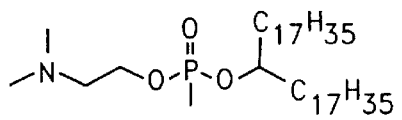
FIG. 7 depicts the structure of a cationic lipid, compound 7-1. This compound and its synthesis is described in the commonly assigned and co-pending U.S. patent application, "Novel Methylphosphonate-Based Cationic Lipids", U.S. Ser. No. 08/484,716, filed Jun. 7, 1995, the disclosure of which is incorporated herein by reference.

Prior to setting forth the invention, it may be helpful to an understanding thereof to first set forth definitions of certain terms that will be used herein after. These terms will have the following meanings unless explicitly stated otherwise:

The term "lipophilic moiety" refers to a moiety which demonstrates one or more of the following characteristics: tend to be water insoluble, tend to be soluble in non-polar solvent, tend to favor octanol in octanol/water partition measurements, or tend to be compatible with lipid bilayers and may be bilayer forming.

The phrase "charged moiety" as used in the terms "positively charged moiety" and "negatively charged moiety" refers to a moiety, independent of the cationic lipid for which it is a substituent, having a net positive or negative charge respectively within the pH range of 2 to 12. The net charge for the cationic lipid is the summation of all charged moieties occurring on the lipid, such that the net charge may be positive, neutral or negative.

The term "alkyl" refers to saturated aliphatic groups including straight-chain, branched-chain and cyclic groups. Suitable alkyl groups include, but are not limited to, cycloalkyl groups such as cyclohexyl and cyclohexylmethyl. "Lower alkyl" refers to alkyl groups of 1 to 6 carbon atoms. Fluoroalkyl or perfluoroalkyl refers to singly, partially, or fully fluorinated alkyl groups.

The term "alkenyl" refers to an unsaturated aliphatic group having at least one double bond.

The term "arylamine" refers to aromatic groups that have at least one ring having a conjugated pi electron system and includes carbocyclic aryl, heterocyclic aryl and biaryl groups, all of which may be optionally substituted.

The term "aralkylamine" refers to an alkyl group substituted with an aryl group. Suitable aralkyl groups include benzyl, picolyl, and the like, all of which may be optionally substituted.

The term "aralkyl" refers to an alkyl group substituted with an aryl group. Suitable aralkyl groups include benzyl, picolyl, and the like, all of which may be optionally substituted.

The term "oligonucleoside" or "oligomer" refers to a chain of nucleosides that are linked by internucleoside linkages that is generally from about 4 to about 100 nucleosides in length, but which may be greater than about 100 nucleosides in length. They are usually synthesized from nucleoside monomers, but may also be obtained by enzymatic means. Thus, the term "oligomer" refers to a chain of oligonucleosides that have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a morpholino linkage, a sulfamate linkage, a silyl linkage, a carbamate linkage, an amide linkage, a guanidine linkage, a nitroxide linkage or a substituted hydrazine linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer. Optionally, said non-nucleoside moiety may serve to link other small molecules which may interact with target sequences or alter uptake into target cells. "Lipid aggregate" is a term that includes liposomes of all types both unilamellar and multilamellar as well as micelles and more amorphous aggregates of cationic lipid or lipid mixed with amphipathic lipids such as phospholipids. "Target cell" refers to any cell to which a desired compound is delivered, using a lipid aggregate as carrier for the desired compound.

"Transfection" is used herein to mean the delivery of expressible nucleic acid to a target cell, such that the target cell is rendered capable of expressing said nucleic acid. It will be understood that the term "nucleic acid" includes both DNA and RNA without regard to molecular weight, and the term "expression" means any manifestation of the functional presence of the nucleic acid within the cell, including without limitation, both transient expression and stable expression.

"Delivery" is used to denote a process by which a desired compound is transferred to a target cell such that the desired compound is ultimately located inside the target cell or in, or on the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

All references which have been cited below are hereby incorporated by reference in their entirety.

The generic structure of functionally active cationic lipids requires three contiguous moities, e.g. cationic-head-group, a linker, and a lipid-tail group. While a wide range of structures can be envisioned for each of the three moieties, it has been demonstrated that there is no a priori means to predict which cationic lipid will successfully transfect anionic-macromolecules into a particular cell line. The property of a cationic lipid to be formulated with an anionic macromolecule which will then successfully transfect a cell line is empirical. We demonstrate the abilities of novel cationic lipids which are chemically linked into multimeric constructions to enhance the uptake of macromolecules.

The novel amide-based cationic lipids of the present invention have the general structure:

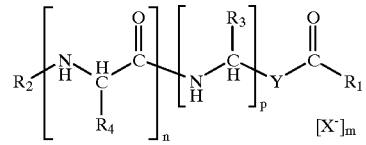

comprising any salt, solvate, or enantiomers thereof. The symbols $R_1$, $R_2$, $R_3$, $R_4$, Y, X, n, and m are described as follows; $R_1$ represents the lipid-tail group of the amide-based cationic lipid and may be hydrogen or a variety of lipophilic moieties, in particular, these include for example, a straight chain alkyl of 1 to about 24 carbon atoms, a straight chain alkenyl of 2 to about 24 carbon atoms, a symmetrical branched alkyl or alkenyl of about 10 to about 50 carbon atoms, a unsymmetrical branched alkyl or alkenyl of about 10 to about 50 carbon atoms, a amine derivative, a steroidyl moiety, a glyceryl derivative, and $OCH(R_5R_6)$ or $N(R_5R_6)$, wherein $R_5$ and $R_6$ are straight chain or branched alkyl moieties of about 10 to about 30 carbon atoms.

When $R_1$ is an amine derivative a variety of such derivatives may be utilized, for example, a straight chain alkylamine moiety of 1 to about 24 carbon atoms, a straight chain alkenylamine moiety of 2 to about 24 carbon atoms, a symmetrical branched alkylamine or alkenylamine moiety of about 10 to about 50 carbon atoms, a unsymmetrical branched alkylamine or alkenylamine moiety of about 10 to about 50 carbon atoms, cyclic amine moiety of about 3 to about 10 carbon atoms, or a steroidyl moiety.

In the case where $R_1$ is a steriodal moiety a variety of such moieties may be utilized including for example pregnenolone, progesterone, cortisol, corticosterone, aldosterone, androstenedione, testosterone, or cholesterol or analogs thereof.

$R_2$ represents the cationic head group of the amide-based cationic lipid and may be a positively charged moiety independent of $R_3$ and $R_4$. In such case, $R_2$ may be an amino acid residue having a unsubstituted or substituted positively charged side chain. Where the amino acid residue is substituted the substituent may be an alkyl of 1 to about 6 carbon atoms or a substituent which renders a secondary, tertiary, or quaternary amine having an alkyl moiety of 1 to about 6 carbon atoms which is substituted with a hydroxyl, an amino, an alkoxy of 1 to about 6 carbon atoms, an alkylamino of 1 to about 6 carbon atoms, or a dialkylamino of 2 to about 12 carbon atoms.

In particular, when $R_2$ is an amino acid residue it may be, for example, lysine, arginine, histidine, ornithine, or an amino acid analog. Specific examples of amino acid analogs include 3-carboxyspermidine, 5-carboxyspermidine, 6-carboxyspermine and a monoalkyl, dialkyl, or peralkyl substituted derivative which is substituted on one or more amine nitrogens with an alkyl group of 1 to about 6 carbon atoms.

$R_2$, $R_3$, and $R_4$ may be positively charged moieties, or at least one but not all of $R_2R_3$, or $R_4$ may be a positively charged moiety. In the latter case, the remaining R group(s) may independently be a hydrogen, a substituted or unsubstituted is alkyl moiety of 1 to about 6 carbon atoms, or a substituted or unsubstituted heterocyclic moiety of about 5 to about 10 carbon atoms. More specifically, these groups may be substituted with a hydroxyl, a thio, an aryl of 1 to about 20 carbon atoms, or $OR_7$, wherein $R_7$ is an alkyl moiety of 1 to about 24 carbon atoms, an alkenyl of 2 to about 24 carbon atoms, an aryl of about 5 to about 20 carbon atoms or an aralkyl of about 6 to about 25 carbon atoms.

When $R_2$, $R_3$, and $R_4$ are positively charged moieties they may independently be, for example, an alkylamine moiety, a fluoroalkylamine moiety, or a perfluoroalkylamine moiety of 1 to about 6 carbon atoms, an arylamine moiety or an aralkylamine moiety of 5 to about 10 carbon atoms, a guanidinium moiety, an enamine moiety, a cyclic amine moiety, an amidine moiety, an isothiourea moiety, a heterocyclic amine moiety, or a substituted heterocyclic moiety or a substituted alkyl moiety of 1 to about 6 carbon atoms substituted with a substituent selected from the group consisting of $NH_2$, $C(=O)NH_2$, $NHR_7$, $C(=O)NHR_7$, $NHR_7R_8$, and $C(=O)NHR_7R_8$, wherein $R_7$ and $R_8$ are independently selected from an alkyl moiety of 1 to about 24 carbon atoms, an alkenyl moiety of 2 to about 24 carbon atoms, an aryl moiety of about 5 to about 20 carbon atoms, and an aralkyl moiety of about 6 to about 25 carbon atoms. In particular, when at least $R_2$, $R_3$, or $R_4$ is an arylamine moiety a variety of such moieties may be utilized including, for example, tryptophane, phenylanaline, and tyrosine.

$R_3$ and $R_4$ may also be independently a lipophilic moiety or a negatively charged moiety. In particular, when $R_3$ and/or $R_4$ is a lipophilic moiety it may be a straight chain alkyl moiety of about 3 to about 24 carbon atoms, a straight chain alkenyl moiety of 2 to about 24 carbon atoms, a symmetrical branched alkyl or alkenyl moiety of about 10 to about 50 carbon atoms, a unsymmetrical branched alkyl or alkenyl moiety of about 10 to about 50 carbon atoms, an aryl moiety of about 5 to about 20 carbon atoms, an aralkyl moiety of about 6 to about 25 carbon atoms, or a steroidyl moiety.

In the case when $R_3$ and/or $R_4$ is a negatively charged moiety it may be a carboxyalkyl moiety, a phosphonoalkyl moiety, a sulfonoalkyl moiety, or a phosphatidylalkyl moiety of 1 to about 24 carbon atoms.

The linker comprises the structure joining the head group, $R_1$ to the lipid-tail group, $R_2$. This structure includes Y may be a direct link from —(C=O)— to —(CHR$_3$)— or an alkylene of 1 to about 20 carbon atoms.

n and p are integers indicating the number of repeating units enclosed by the brackets and having magnitudes independent from each other ranging from 0 to 8, such that the sum of n and p is from 1 to 16, in particular cases the sum of the integers range from 1 to 4 and in specific instances from 1 to 2.

The counterion represented by $X^-$ is an anion or a polyanion that binds to the positively charged groups present on the phosphonic acid-based cationic lipid via charge-charge interactions. When these cationic lipids are to be used in vivo the anion or polyanion should be pharmaceutically acceptable.

m is an integer indicating the number of anions or polyanions associated with the cationic lipid. In particular this integer ranges in magnitude from 0 to a number equivalent to the positive charge(s) present on the lipid.

In particular, when Y is a direct link and the sum of n and p is 1, then one or either $R_3$ or $R_4$ must comprise an alkyl moiety of at least 10 carbon atoms.

The cationic lipids of the present invention include salts, solvates, or enatiomeric isomers resulting from any or all asymmetric atoms present in the lipid. Included in the scope of the invention are racemic mixtures, diastereomeric mixtures, optical isomers or synthetic optical isomers which are isolated or substantially free of their enantiomeric or diasteriomeric partners. The racemic mixtures may be separated into their individual, substantially optically pure isomers by techniques known in the art, such as, for example, the separation of diastereomeric salts formed with optically active acid or base adjuncts followed by conversion back to the optically active substances. In most instances, the desired optical isomer is synthesized by means of stereospecific reactions, beginning with the appropriate stereoisomer of the desired starting material. Methods and theories used to obtain enriched and resolved isomers have been described (Jacques et al., "Enantiomers, Racemates and Resolutions." Kreiger, Malabar, Fla., 1991).

The salts include pharmaceutically or physiologically acceptable non-toxic salts of these compounds. Such salts may include those derived by combination of appropriate cations such as alkali and alkaline earth metal ions or ammonium and quaternary amino ions with the acid anion moiety of the phosphate or phosphorothioate acid group present in polynucleotides. Suitable salts include for example, acid addition salts such as HCl, HBr, HF, HI, $H_2SO_4$, and trifluoroacetate. The salts may be formed from acid addition of certain organic and inorganic acids, e.g., HCl, Hbr, $H_2SO_4$, amino acids or organic sulfonic acids, with basic centers, (e.g. amines), or with acidic groups. The composition herein also comprise compounds of the invention in their un-ionized, as well as zwitterionic forms.

Exemplary invention cationic lipids have the structures shown in the Summary of the Invention above.

The cationic lipids form aggregates with polyanionic macromolecules such as oligonucleotides, oligomers, peptides, or polypeptides through attraction between the positively charged lipid and the negatively charged polyanionic macromolecule. The aggregates may comprise multiamellar or unilamellar liposomes or other particles. Hydrophobic interactions between the cationic lipids and the hydrophobic substituents in the polyanionic macromolecule such as aromatic and alkyl moieties may also facilitate aggregate formation. Cationic lipids have been shown to efficiently deliver nucleic acids and peptides into cells and are suitable for use in vivo or ex vivo.

Cationic lipid-polyanionic macromolecule aggregates may be formed by a variety of methods known in the art. Representative methods are disclosed by Felgner et al., supra; Eppstein et al. supra; Behr et al. supra; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization is used when consistently small (50 to 200 nm) and relatively uniform aggregates are desired (Mayhew, E., supra). In general aggregates may be formed by preparing lipid particles consisting of either (1) a cationic lipid of the invention or (2) a cationic lipid mixed with a colipid, followed by adding a polyanionic macromolecule to the lipid particles at about room temperature (about 18 to 26° C.). In general, conditions are chosen that are not conducive to deprotection of protected groups. The mixture is then allowed to form an aggregate over a period of about 10 minutes to about 20 hours, with about 15 to 60 minutes most conveniently used. The complexes may be formed over a longer period, but additional enhancement of transfection efficiency will not usually be gained by a longer period of complexing. Colipids may be neutral or synthetic lipids having no net charge or a positive or a negative charge. In particular, natural colipids that are suitable for preparing lipid aggregates with the cationic lipids of the present invention are dimyristoylphosphatidylethanolamine, dipalmitoylphosphatidylethanolamine, palmitoyloleolphosphatidylethanolamine, cholesterol, distearoyalphosphatidylethanolamine, phosphatidylethanolamine covalently linked to polyethylene glycol and mixtures of these colipids.

The optimal cationic lipid:colipid ratios for a given cationic lipid is determined by mixing experiments to prepare lipid mixtures for aggregation with a polyanionic macromolecule using cationic lipid:colipid ratios between about 1:0.1 and 1:10. Methods to determine optimal cationic lipid:colipid ratios have been described (see, Felgner, infra). Each lipid mixture is optionally tested using more than one oligonucleotide-lipid mixture having different nucleic acid:lipid molar ratios to optimize the oligonucleotide:lipid ratio.

Suitable molar ratios of cationic lipid:colipid are about 0.1:1 to 1:0.1, 0.2:1 to 1:0.2, 0.4:1 to 1:0.4, or 0.6:1 to 1:0.6. Lipid particle preparation containing increasing molar proportions of colipid have been found to enhance oligonucleotide transfection into cells with increasing colipid concentrations. In addition, the cationic lipids can be used together in admixture, or different concentrations of two or more cationic lipids in admixture, with or without colipid. Liposomes or aggregates maybe conveniently prepared by first drying the lipids in solvent (such as chloroform) under reduced pressure. The lipids may then be hydrated and converted to liposomes or aggregates by adding water or low ionic strength buffer (usually less than about 200 mM total ion concentration) followed by agitating (such as vortexing and/or sonication) and/or freeze/thaw treatments. The size of the aggregates or liposomes formed range from about 40 nm to 600 nm in diameter.

The amount of an oligonucleotide delivered to a representative cell by at least some of the cationic lipids was found to be significantly greater than the amount delivered by commercially available transfection lipids. The amount of oligonucleotide delivered into cells was estimated to be about 2- to 100-fold greater for the cationic lipids of the invention based on the observed fluorescence intensity of transfected cells after transfection using a fluorescently labeled oligonucleotide. The cationic lipids described herein also transfect some cell types that are not detectably transfected by commercial lipids. Functionality of cationic lipid-DNA aggregates was demonstrated by assaying for the gene product of the exogenous DNA. Similarly, the functionality of cationic lipid-oligonucleotide aggregates were demonstrated by antisense inhibition of a gene product.

The cationic lipids described herein also differed from commercially available lipids by efficiently delivering an oligonucleotide into cells in tissue culture over a range of cell confluency from about 50 to 100%. Most commercially available lipids require cells that are at a relatively narrow confluency range for optimal transfection efficiency. For example, Lipofectin™ requires cells that are 70–80% confluent for transfecting the highest proportion of cells in a population. The cationic lipids described herein may be used to transfect cells that are about 10–50% confluent, but toxicity of the lipids was more pronounced, relative to that seen using cells that are about 50–100% confluent. In general, the cationic lipids transfected cells that were about 60–100% confluent with minimal toxicity and optimal efficiency. Confluency ranges of 60–95% or 60–90% are thus convenient for transfection protocols with most cell lines in tissue culture.

The cationic lipid aggregates were used to transfect cells in tissue culture and the RNA and the DNA encoded gene products were expressed in the transfected cells.

The cationic lipid aggregates may be formed with a variety of macromolecules such as oligonucleotides and oligomers. Oligonucleotides used in aggregate formation may be single stranded or double stranded DNA or RNA, oligonucleotide analogs, and plasmids.

In general, relatively large oligonucleotides such as plasmids or mRNAs will carry one or more genes that are to be expressed in a transfected cell, while comparatively small oligonucleotides will comprise (1) a base sequence that is complementary (via Watson Crick or Hoogsteen binding) to a DNA or RNA sequence present in the cell or (2) a base sequence that permits oligonucleotide binding to a molecule inside a cell such as a peptide, protein, or glycoprotein. Exemplary RNAs include ribozymes and antisense RNA sequences that are complementary to a target RNA sequence in a cell.

An oligonucleotide may be a single stranded unmodified DNA or RNA comprising (a) the purine or pyrimidine bases guanine, adenine, cytosine, thymine and/or uracil: (b) ribose or deoxyribose; and (c) a phosphodiester group that linkage adjacent nucleoside moieties. Oligonucleotides typically comprise 2 to about 100 linked nucleosides. Typical oligonucleotides range in size from 2–10, 2–15, 2–20, 2–25, 2–30, 2–50, 8–20, 8–30 or 2–100 linked nucleotides. oligonucleotides are usually linear with uniform polarity and, when regions of inverted polarity are present, such regions comprise no more than one polarity inversion per 10 nucleotides. One inversion per 20 nucleotides is typical. Oligonucleotides can also be circular, branched or double-stranded. Antisense oligonucleotides generally will comprise a sequence of about from 8–30 bases or about 8–50 bases that is substantially complementary to a DNA or RNA base sequence present in the cell. The size of oligonucleotide that is delivered into a cell is limited only by the size of polyanionic macromolecules that can reasonably be prepared and thus DNA or RNA that is 0.1 to 1 Kilobase (Kb), 1 to 20 Kb, 20 Kb to 40 Kb or 40 Kb to 1,000 Kb in length may be delivered into cells.

Oligonucleotides also include DNA or RNA comprising one or more covalent modifications. Covalent modifications include (a) substitution of an oxygen atom in the phosphodiester linkage of an polynucleotide with a sulfur atom, a methyl group or the like, (b) replacement of the phosphodiester group with a nonphosphorus moiety such as —O—CH$_2$O—, —S—CH$_2$O— or —O—CH$_2$O —S, and (c) replacement of the phosphodiester group with a phosphate analog such as —O— P(S)(O)—O, —O—P(S)(S)—O—, —O—P(CH$_3$)(O)—O or —O—P(NHR$^{10}$) (O)—O— where R$^{10}$ is alkyl of 1 to about 6 carbon atoms, or an alkyl ether of 1 to about 6 carbon atoms. Such substitutions may constitute from about 10% to 100% or about 20% to about 80% of the phosphodiester groups in unmodified DNA or RNA. Other modifications include substitutions of or on sugar moiety such as morpholino, arabinose 2'-fluororibose, 2'-fluoroarabinose, 2'-O-methylribose, or 2'-O-allylribose. Oligonucleotides and methods to synthesize them have been described (for example see PCT/US90/03138, PCT/US90/06128, PCT/US90/06090, PCT/US90/06110, PCT/US92/03385, PCT/US91/08811, PCT/US91/03680, PCT/US91/06855, PCT/US91/01141, PCT/US92/10115, PCT/US92/10793, PCT/US93/05110, PCT/US93/05202, PCT/US92/04294, WO 86/05518, WO 89/12060, WO 91/08213, WO 90/15065, WO 91/15500, WO 92/02258, WO 92/20702, WO 92/20822, WO 92/20823, U.S. Pat. No. : 5,214,136 and Uhlmann *Chem Rev.* 90:543, 1990).

The linkage between the nucleotides of the oligonucleotide may be a variety of moieties including both phosphorus-containing moieties and non phosphorus-containing moieties such as formacetal, thioformacetal, riboacetal and the like. A linkage usually comprises 2 or 3 atoms between the 5' position of a nucleotide and the 2' or 3' position of an adjacent nucleotide. However, other synthetic linkers may contain greater than 3 atoms.

The bases contained in the oligonucleotide may be unmodified or modified or natural or unatural purine or pyrimidine bases and may be in the α or β anomer form. Such bases may be selected to enhance the affinity of oligonucleotide binding to its complementary sequence relative to bases found in native DNA or RNA. However, it is preferable that modified bases are not incorporated into an oligonucleotide to an extent that it is unable to bind to complementary sequences to produce a detectably stable duplex or triplex.

Exemplary bases include adenine, cytosine, guanine, hypoxanthine, inosine, thymine, uracil, xanthine, 2-aminopurine, 2,6-diaminopurine, 5-(4-methylthiazol-2-yl) uracil, 5-(5-methylthiazol-2-yl)uracil, 5-(4-methylthiazol-2-yl)cytosine, 5-(5-methylthiazol-2-yl)cytosine and the like. Other exemplary bases include alkylated or alkynylated bases having substitutions at, for example, the 5 position of pyrimidines that results in a pyrimidine base other than uracil, thymine or cytosine, (i.e., 5-methylcytosine, 5-(1-propynyl)cytosine, 5-(1-butynyl)cytosine, 5-(1-butynyl) uracil, 5-(1-propynyl)uracil and the like). The use of modified bases or base analogs in oligonucleotides have been previously described (see PCT/US92/10115; PCT/US91/08811; PCT/US92/09195; WO 92/09705; WO 92/02258; Nikiforov, et al., *Tet. Lett.* 33:2379, 1992; Clivio, et al., *Tet. Lett.* 33:65, 1992; Nikiforov, et al., *Tet. Lett.* 32:2505, 1991; Xu, et al., *Tet. Lett.* 32:2817, 1991; Clivio, et al., *Tet. Lett.* 33:69, 1992; and Connolly, et al., *Nucl. Acids Res.* 17:4957, 1989).

Aggregates may comprise oligonucleotides or oligomers encoding a therapeutic or diagnostic polypeptide. Examples of such polypeptides include histocompatibility antigens, cell adhesion molecules, cytokines, antibodies, antibody fragments, cell receptor subunits, cell receptors, intracellular enzymes and extracellular enzymes or a fragment of any of these. The oligonucleotides also may optionally comprise expression control sequences and generally will comprise a transcriptional unit comprising a transcriptional promoter, an enhancer, a transcriptional terminator, an operator or other expression control sequences.

Oligonucleotides used to form aggregates for transfecting a cell may be present as more than one expression vector. Thus, 1, 2, 3, or more different expression vectors may be delivered into a cell as desired. Expression vectors will typically express 1, 2, or 3 genes when transfected into a cell, although many genes may be present such as when a herpes virus vector or a artificial yeast chromosome is delivered into a cell. Expression vectors may further encode selectable markers (e.g. neomycin phosphotransferase, thymidine kinase, xanthine-guanine phosphoribosyltransferase, and the like) or biologically active proteins such as metabolic enzymes or functional proteins (e.g. immunoglobulin genes, cell receptor genes, cytokines (e.g. IL-2, IL-4, GM-CSF, γ-INF and the like), or genes that encode enzymes that mediate purine or pyrimidine metabolism and the like)).

The nucleic acid sequence of the oligonulcleotide coding for specific genes of interest may be retrieved, without undue experimentation, from the GenBank of EMBL DNA libraries. Such sequences may include coding sequences, for example, the coding sequences for structural proteins, hormones, receptors and the like, and the DNA sequences for other DNAs of interest, for example, transcriptional and translational regulatory elements (promoters, enhancers, terminators, signal sequences and the like), vectors (integrating or autonomous) and the like. Non-limiting examples of DNA sequences which may be introduced into cells include those sequences coding for fibroblast growth factor (see WO 87/01728); ciliary neurotrophic factor (Lin et al., *Science*, 246:1023, 1989); human interferon-α receptor (Uze, et al., *Cell*, 60:225, 1990); the interleukins and their receptors (reviewed in Mizal, *FASEB J.*, 3:2379, 1989); hybrid interferons (see EPO 051,873); the RNA genome of human rhinovirus (Callahan, *Proc. Natl. Acad. Sci.*, 82:732, 1985); antibodies including chimeric antibodies (see U.S. Pat. No. : 4,816,567); reverse transcriptase (see Moelling, et al., *J. Virol.*, 32:370, 1979); human CD4 and soluble forms thereof (Maddon et al., *Cell*, 47:333, 1986), WO 88/01304 and WO 89/01940); and EPO 330,191, which discloses a rapid immunoselection cloning method useful for the cloning of a large number of desired proteins.

Aggregates can be used in antisense inhibition of gene expression in a cell by delivering an antisense oligonucleotide into the cell (see Wagner, *Science* 260:1510, 1993 and WO 93/10820). Such oligonucleotides will generally comprise a base sequence that is complementary to a target RNA sequence that is expressed by the cell. However, the oligonucleotide may regulate intracellular gene expression by binding to an intracellular nucleic acid binding protein (see Clusel, *Nucl. Acids Res.* 21:3405, 1993) or by binding to an intracellular protein or organelle that is not known to bind to nucleic acids (see WO 92/14843). A cell that is blocked for expression of a specific gene(s) is useful for manufacturing and therapeutic applications. Exemplary manufacturing uses include inhibiting protease synthesis in a cell to increase production of a protein for a therapeutic or diagnostic application (e.g., reduce target protein degradation caused by the protease). Exemplary therapeutic applications include inhibiting synthesis of cell surface antigens to reduce rejection and/or to induce immunologic tolerance of the cell either after it is implanted into a subject or when the cell is trnsfected in vivo (e.g. histocompatibility antigens, such as MHC class II genes, and the like).

Methods to introduce aggregates into cells in vitro and in vivo have been previously described (see U.S. Pat. Nos.: 5,283,185 and 5,171,678; WO 94/00569; WO 93/24640; WO 91/16024; Felgner, *J. Biol Chem* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Entry of liposomes or aggregates into cells may be by endocytosis or by fusion of the liposome or aggregate with the cell membane. When fusion takes place, the liposomal membrane is integrated into the cell membrane and the aqueous contents of the liposome merge with the fluid in the cell.

Endocytosis of liposomes occurs in a limited class of cells; those that are phagocytic, or able to ingest foreign particles. When phagocytic cells take up liposomes or aggregates, the cells move the spheres into subcellular organelles known as lysosomes, where the liposomal membranbes are thought to be degraded. From the lysosome, the liposomal lipid components probably migrate outward to become part of cell's membranes and other liposomal components that resist lysosomal degradation (such as modified oligonucleotides or oligomers) may enter the cytoplasm.

Lipid fusion involves the transfer of individual lipid molecules from the liposome or aggregate into the plasma membrane (and vice versa); the aqueous contents of the liposome may then enter the cell. For lipid exchange to take place, the liposomal lipid must have a particular chemistry in relation to the target cell. Once a liposomal lipid joins the cell membrane it can either remain in the membrane for a period of time or be redistributed to a variety of intracellular membranes. The cationic lipids of the present invention can be used to deliver an expression vector into a cell for manufacturing or therapeutic use. The expression vectors can be used in gene therapy protocols to deliver a therapeutically useful protein to a cell or for delivering nucleic acids encoding molecules that encode therapeutically useful proteins or proteins that can generate an immune response in a host for vaccine or other immunomodulatory purposes according to known methods (see U.S. Pat. Nos.: 5,399,346 and 5,336,615, WO 94/21807 and WO 94/12629). The vector-transformed cell can be used to produce commercially useful cell lines, such as a cell line for producing therapeutic proteins or enzymes (e.g. erythropoietin, and the like), growth factors (e.g. human growth hormone, and the like) or other proteins. The aggregates may be utilized to develop cell lines for gene therapy applications in humans or other species including murine, feline, bovine, equine, ovine or non-human primate species. The aggregates may be to deliver polyanionic macromolecules into cells in tissue culture medium in vitro or in an animal in vivo.

The following examples are offered by way of illustration and not by way of limitation.

EXAMPLES

General Methods

All reactions were run under a positive pressure of dry argon. Reactions requiring anhydrous conditions were performed in flame-dried glassware which was cooled under argon. Tetrahydrofuran (THF, Aldrich Milwaukee, Wis.) was distilled from potassium/benzophenone ketyl immediately prior to use. Methylene chloride, pyridine, toluene, heptane, methanol, and ethanol were obtained as anhydrous reagent (<0.005% water) or reagent grade and were used without further purification. TLC was performed on 0.2 mm E. Merck precoated silica gel 60 $F_{254}$ TLC plates (20×20 cm aluminum sheets, Fisher, Pittsburgh, Pa). Flash chromatography was performed using E. Merck 230–400 mesh silica gel. All $^1$H, $^{13}$C and $^{31}$P NMR spectra were recorded on a 300 MHz Bruker ARX Spectrometer (Bruker, Boston, Mass.) and were obtained in $CDCl_3$ unless otherwise indicated. Mass spectra were provided by The Scripps Research Institute Mass Spectrometry Facility of La Jolla, Calif. FAB mass spectra were obtained on a FISONS VG ZAB-VSE double focusing mass spectrometer equipped with a cesium ion gun (Fisions, Altrincham, UK). ESI mass spectra were obtained on an API III PE Sciex triple-quadrupole mass spectrometer (Sciex, Toronto, Calif.).

Example 1

Synthesis of L-Ornithylglycyl-N-(1-heptadecyloctadecyl)glycinamide, Dihydrotrifluoroacetate (1–9) and $N^2,N^5$-Bis(3-aminopropyl)-L-ornithylglycyl-N-(1-heptadecyloctadecyl)glycinamide, Tetrahydrotrifluoroacetate (1–10)

Synthesis of Stearone oxime (1–1) was prepared as follows and used without further purification. A 500 mL, round-bottomed reaction flask equipped with a magnetic stirrer, reflux condenser, and an argon inlet tube was charged with stearone (12.3 g, (24.3 mmol)), hydroxylamine hydrochloride (8.5 g, (121.6 mmol)), pyridine (12.0 mL, (148.4 mmol)), and ethanol (125 mL). After the mixture was refluxed for 2 hours it was cooled to room temperature and left standing overnight. The resulting white solid was collected, washed with water and then with ethanol, air-dried for 30 minutes, and then dried under vacuum (0.5 mm Hg) at room temperature for 15 hours to afford 11.59 g (91% yield) of compound 1-1 as a white solid: mp 68–69° C. (lit. (Grun et al., *Angew. Chem.* 39, 421, 1926) mp 66–67° C.); $R_f$ 0.49 (9:1 heptane:ethyl acetate); $^1$H NMR $\delta$7.40 (br s, 1 H), 2.32 (t, J=7.8 Hz, 2 H), 2.15 (t, J=7.8 Hz, 2 H), 1.49 (m, 4 H), 1.25(br s, 56 H), 0.88 (t, J=6.5 Hz, 6 H).

Synthesis of 18-Pentatriacontanamine (1-2) was prepared as follows and used without further purification. A Parr bottle was charged with stearone oxime (5.0 g, (9.6 mmol)), 50 mL of a 1:1 mixture of methylene chloride:methanol, and 1 g of wet Raney nickel (washed with 95% ethanol to remove water). The reaction bottle was placed in a Parr shaker apparatus, filled with $H_2$ gas and evacuated by vacuum to remove air, and then subjected to 45 psi $H_2$ gas at room temperature with shaking for 15 hours. The reaction mixture was then filtered and washed with 1:1 methylene chloride:methanol. The filtrate was concentrated by rotary evaporation and the crude product was purified by flash chromatography on silica gel (100 g) using 95:5 methylene chloride:methanol to afford 1.99 g (41% yield) of 1-2 as a white solid and 1.22 g of a mixture (ratio not determined) of 1-2 and stearone. Coumpound 1-2 gave the following spectral data: $R_f$ 0.58 (4:1 methylene chloride:methanol); $^1$H NMR $\delta$7.50–6.70 (br s, 2 H), 3.03 (apparent quintet, J=6.3 Hz, 1 H), 1.62–1.05 (m, 64 H), 0.88 (t, J=6.6 Hz, 6 H); MS (ESI) m/z 509 (MH$^+$).

Synthesis N-Carbobenzyloxyglycylglycine (1-3) was prepared as follows and used without further purification. A 250 mL round-bottomed reaction flask equipped with a magnetic stirrer was charged with glycylglycine (1.0 g, (7.6 mmol)), aqueous sodium hydroxide (8.3 mL of a 2 M solution, (16.6 mmol)), water (2.0 mL) and toluene (5.0 mL). The resulting biphasic mixture was cooled in an ice-water bath and then benzyl chloroformate (1.2 mL, (8.3 mmol)) was added to the reaction mixture dropwise via syringe. The reaction mixture was allowed to warm to room temperature and stirred for 3 hours. The reaction mixture was then transferred to a separatory funnel and extracted with ethyl acetate. The phases were separated and the aqueous phase was acidified to pH 2–3 by dropwise addition of a 6 N aqueous HCl solution. The acidified aqueous phase was placed in a refrigerator for 30 minutes. The resulting white solid was collected, air-dried and then vacuum-dried to afford 1.21 (60% yield) of compound 1-3 as a white solid. $R_f$ 0.44 (1:1 methylene chloride:methanol); $^1$H NMR (CD$_3$OD) δ 7.39–7.27 (m, 5 H), 5.10 (s, 2 H), 3.97 (s, 2 H), 3.82 (s, 2 H).

Synthesis of (Carbobenzyloxy)glycyl-N-(1heptadecyloctadecyl)glycinamide (1-4) was prepared as follows and used without further purification. A 100 mL round bottomed reaction flask equipped with a magnetic stirrer was charged with N-carbobenzyloxyglycylglycine (0.21 g, (0.78 mmol)), 18-pentatriacontanamine (1-2) (0.40 g, (0.78 mmol)), dicyclo-hexylcarbodiimide (0.18 g, (0.86 mmol)), 1-hydoxybenzotriazole hydrate (0.12 g, (0.86 mmol)) and THF (10 mL). The reaction mixture was stirred at room temperature under argon for 15 hours. The reaction mixture was filtered and washed with ethyl acetate. The filtrate was concentrated by rotary evaporation and the crude product was purified by flash chromatography on silica gel using 1:1 ethyl acetate-heptane to afford 0.39 g (66% yield) of compound 1-4 as a white solid. $R_f$ 0.22 (1:1 ethyl acetate-heptane); $^1$H NMR δ7.15 (t, J=4.5 Hz, 1 H), 6.18 (d, J=9.6 Hz, 1 H), 5.74 (t, J=4.5 Hz, 1 H), 5.10 (s, 2 H), 3.90 (m, 5 H), 2.20–1.00 (m, 64 H), 0.88 (t, J=6.6 Hz, 6 H); MS (FAB) m/z 757 (MH$^+$).

Synthesis of Glycyl-N-(1-heptadecylocta decyl)-glycinamide (1-5) was prepared as follows and used without further purification. A Parr bottle was charged with N-(carbobenzyloxy)glycyl-N-(1-heptadecyloctadecyl) glycinamide (1-4) (2.95 g, (3.9 mmol)), palladium on carbon (0.5 g, 5% Pd content), and 50 mL of a 9:1 mixture of methylene chloride:methanol. The reaction bottle was secured in a Parr shaker apparatus, filled with H$_2$ gas, evacuated by vacuum twice to remove oxygen, and then subjected to 50 psi H$_2$ gas, with shaking, at room temperature for 10 hours. The reaction mixture was filtered through a filter agent and washed with 1:1 methylene chloride:methanol to remove catalyst. The filtrate was concentrated by rotary evaporation to afford 1.75 g (72% yield) of compound 1-5 as a white solid. $R_f$ 0.42 (4:1 methylene chloride-methanol); $^1$H NMR δ7.88 (br s, 1 H), 5.85 (br d, J=10.8 Hz, 1 H), 4.02–3.79 (m, 3 H), 3.40 (br s, 2 H), 1.69 (br s, 3 H), 1.58–0.98 (m, 63 H), 0.88 (t, J=6.5 Hz, 6 H).

Synthesis of N$^2$,N$^5$-Bis[(1,1-dimethylethoxy)carbonyl]-N$^2$,N$^5$-bis[3-[(1,1-dimethylethoxy) carbonyl]aminopropyl]-L-ornithine, N-hydroxysuccinimydyl ester (1-6) was prepared as follows and used without further purification. A 100 mL round-bottomed reaction flask was charged with N$^2$,N$^5$-Bis[(1,1-dimethylethoxy)carbonyl]-N$^2$,N$^5$-bis[3-[(1,1-dimethylethoxy)carbonyl]aminopropyl]-L-ornithine (Behr, Acc. Chem. Res. 26:274, 1993; (2.08 g, (3.2 mmol)), dicyclohexylcarbodiimide (0.73 g, (3.5 mmol)), N-hydroxysuccinimide (0.41 g, (3.5 mmol)), and methylene:chloride (20 mL). The reaction mixture was stirred for 5 hours and then placed in a refrigerator (0–5° C.) overnight. The mixture was filtered and washed with methylene chloride. The filtrate was concentrated by rotary vaporation and the crude product was purified by flash chromatography on silica gel using 1:1 ethyl acetate-heptane to provide 1.2 g (50% yield) of compound 1-6 as a white solid. $^1$H NMR δ5.26 (br s, 1 H), 4.77 (br s, 1 H), 4.28 (br s, 1 H), 3.22–3.09 (m, 10 H), 2.84 (s, 4 H), 2.05–1.61 (m, 8 H), 1.48 and 1.46 and 1.44 (3 s, 36 H); MS (ESI) m/z 744 (MH$^+$).

Synthesis of N$^2$,N$^5$-Bis-[(1,1-dimethylethoxy)carbonyl]-L-ornithylglycyl-N-(1-heptadecyloctadecyl)glycinamide (1-7) was prepared as follows and used without further purification. A 50-mL round-bottomed reaction flask was charged with glycylglycinamide 1-5 (0.05 g, (0.08 mmol)), N,N$^2$-bis-[(1,1-dimethylethoxy)carbonyl]-L-ornithine, N-hydroxysuccinimidyl ester (0.04 g, (0.09 mmol)), and methylene chloride (3 mL). The reaction was stirred at room temperature for 1 hour. The reaction mixture was concentrated by rotary evaporation and then purified by flash chromatography on silica gel (10 g) using ethyl acetate to afford 0.06 g (80% yield) of compound 1-7 as a white waxy semi-solid. $R_f$ 0.52 (9:1 methylene chloride:methanol); $^1$H NMR δ7.66 (br s, 1 H), 7.43 (br s, 1 H), 6.43 (br s, 1 H), 5.55 (br s, 1 H), 4.87 (br s, 1 H), 4.21 (br s, 1 H), 4.07–3.77 (m, 4 H), 3.31–3.02 (m, 2 H), 2.35 (br s, 1 H), 1.93–1.00 (m, 68 H) 1.43 (s, 18 H), 0.88 (t, J=6.6 Hz, 6 H).

Synthesis of N$^2$,N$^5$-Bis[(1,1-dimethylethoxy)carbonyl]-N$^2$,N$^5$-Bis[3-[(1,1-dimethylethoxy)carbonyl]aminopropyl]-L-ornithylglycyl-N-(1-heptadecyloctadecyl)glycinamide (1-8) was prepared as follows and used without further purification. A 50-mL round-bottomed reaction flask was charged with glycylglycinamide 1-5 (0.05 g, (0.08 mmol)), N$^2$,N$^5$-bis[((1,1-dimethylethoxy)carbonyl]-N$^2$,N$^5$-bis[3-[(1,1-dimethylethoxy)carbonyl]aminopropyl]-L-ornithine, N-hydroxysuccinimydyl ester (1-6) (0.07 g, (0.09 mmol)), and methylene chloride (3 mL). The reaction was stirred at room temperature for 1 hour. The reaction mixture was concentrated by rotary evaporation and then purified by flash chromatography on silica gel (10 g) using ethyl acetate to afford 0.055 g (55% yield) of compound 1-8 as a colorless thick oil: $R_f$ 0.57 (9:1 methylene chloride:methanol); $^1$H NMR δ$^1$H NMR δ7.87–7.57 (m, 2 H), 6.48 (m, 1 (m, 6 H), 3.37–2.92 (m, 10 H), 2.38–0.98 (m, 72 H), 1.45 (s, 36 H), 0.88 (t, J=6.6 Hz, 6 H); MS (ESI) m/z 1251 (MH$^+$).

Compound 1-9 was synthesized according to the following procedure. To a 50-mL round-bottomed reaction flask containing glycylglycinamide 1-7 (0.07 g, (0.08 mmol)) was added methylene chloride (2.0 mL) and to this suspension was added trifluoroacetic acid (0.5 mL). The reaction mixture became a homogeneous yellow solution and was left standing for 20 minutes. The reaction mixture was concentrated by rotary evaporation and then coevaporated with heptane (3×10 mL). The resulting residue was subjected to high vacuum (0.1 mm Hg) at room temperature for 15 hours to afford 0.07 g (97% yield) of compound 1-9 as a pale yellow waxy solid: $^1$H NMR (CD$_3$OD) δ7.72 (d, J=9.0 Hz, 1 H), 4.13 and 4.07 and 3.94 and 3.88 (4 s, amide rotamers, 4 H), 3.95–3.82 (m, 2 H), 2.97 (m, 2 H), 1.95–1.76 (m, 4 H), 1.48–1.27 (m, 64 H), 0.89 (t, J=6.6 Hz, 6 H) ; MS (ESI) m/z 694 (MH$^+$).

Compound 1-10 was synthesized according to the following procedure. To a 50-mL round-bottomed reaction flask containing glycylglycinamide 1-8 (0.06 g, (0.04 mmol)) was added methylene chloride (2.0 mL) and to this suspension was added trifluoroacetic acid (0.5 mL). The reaction mixture became a homogeneous yellow solution and was left standing for 20 minutes. The reaction mixture was concentrated by rotary evaporation and then coevaporated with heptane (3×10 mL). The resulting residue was subjected to high vacuum (0.1 mm Hg) at room temperature for 15 hours to afford 0.06 g (99% yield) of compound 1-10 as a pale yellow waxy solid: $^1$H NMR (CD$_3$OD) d 7.72 (d, J=9.0 Hz, 1 H), 4.03 (s, 2 H), 3.88 (s, 2 H), 4.03– 3.79 (m, 2 H), 3.16–3.02 (m, 10 H), 2.20–1.05 (m, 72 H), 0.89 (t, J=6.6 Hz, 6 H); MS (ESI) m/z 851 (MH$^+$)

Example 2

Synthesis N$^2$-[N$^2$,N$^5$-Bis(3-aminopropyl)-L-ornithyl]-N,N-dioctadecyl-L-glutamine, tetrahydrochloride (2-5)

Synthesis of N$^2$-[(1,1-Dimethylethoxy)carbonyl]-N,N-dioctadecyl-L-glutamine, phenylmethyl ester (2-1) was prepared as follows and used without further purification. To a solution of 5.0 g (14.8 mmol) of Boc-Glu-a-OBn in 75 mL of dry DCM was added 8.5 g (16.3 mmol, 1.1 equivalents) of dioctadecylamine (DODA), 3.4 g (4.6 mmol, 1.1 equivalents) of DCC and 2.0 g of HOBT (14.8 mmol, 1.0 equivalents). The reaction mixture was allowed to stir under argon atmosphere overnight. The precipitated dicyclohexylurea was filtered, the residue was washed with 15 mL of DCM, and the combined filtrate was concentrated under reduced pressure to give a colorless oil. The crude product was purified by chromatography on silica gel (9:1 heptanes/ethyl acetate) to afford 12.5 g (quantitative yield) of compound 2-1 as a colorless oil. R$_f$ 0.28 (4:1 heptanes:ethyl acetate) $^1$HNMR δ: 7.35–7.30 (m, 5H), 5.44–5.42 (broad d, J=6 Hz, 1H), 5.16 (AB q, J=12.3 Hz, 2H), 4.31–4.29 (m, 1H), 3.31–3.21 (m, 2H), 3.13–3.08 (dd, J=8.1, 7.6 Hz, 2H) 2.38–2.01 (m, 4H), 1.50–1.45 (m overlaps s, 13H) 1.26 (br s, 60H), 0.88 (t, J=6 Hz, 3H).

Synthesis of N,N-Dioctadecyl-L-glutamine, phenylmethyl ester, hydrotrifluoroacetate (2-2) was prepared as follows and used without further purification. To a solution of 12.5 (14.8 mmol) N$^2$-[(1,1-dimethylethoxy)carbonyl]-N,N-dioctadecyl-L-glutamine, phenylmethyl ester 2-1 in 70 mL of 1,2-dichloroethane was added 50 mL of TFA. The reaction mixture was allowed to stir at room temperature for 30 minutes and concentrated under reduced pressure. The crude oil obtained was further coevaporated with heptane (4×50 mL) and left to stand under high vacuum overnight to afford 12.7 g (quantitative) of compound 2-2 as a waxy solid. $^1$H NMR (CD,OD) δ: 7.23–7.14 (m, 5H), 5.07 (AB q, J=12.0 Hz, 2H), 3.94 (t, J=6.6 Hz, 1H), 3.11–2.92 (m, 4H), 2.33 (t, J=7.5Hz, 2H), 1.97 (dd, J=6.6, 12.0 Hz, 2H), 1.35–1.31 (m, 4H), 1.08 (m, 60H), 0.69 (t, J=6.6 Hz, 3H).

Synthesis of N$^2$- [N$^2$,N$^5$-Bis[(1,1-dimethylethoxy)carbonyl]-N$^2$,N$^5$-bis[3-[((1,1-dimethylethoxy)-carbonyl)aminopropyl]-L-ornithyl]-N,N-dioctadyl-L-glutamine, phenylmethyl ether (2-3) was prepared as follows and used without further purification. To a solution of N,N-Dioctadecyl-L-glutamine, phenylmethyl ester, hydrotrifluoroacetate, compound 2-2, (3.75 g, 4.4 mmol) in 40 mL of dry DCM, was added triethylamine (10 mL). The reaction mixture was allowed to stir at room temperature for 5 minutes and N$^2$,N$^5$-Bis[(1,1-dimethylethoxy)carbonyl]-N$^2$,N$^5$-bis[3-[(1,1-dimethylethoxy)carbonyl]aminopropyl]-L-ornithine (1-6A) (3.1 g, 4.8 mmol, 1.1 equivalents) was added in one portion followed by DCC (992 mg 4.8 mmol, 1.1 equivalents) and HOBt (300 mg, 2.2 mmol, 0.5 equivalents). The progress of the reaction was followed by TLC (7:3 heptane:ethyl acetate), and was considered was complete after 3 hours. The reaction mixture was concentrated under reduced pressure to give a crude oil that was purified by chromatography on silica gel (7:3 heptane:ethyl acetate) to afford 4.6 g (77% yield) of compound 2-3 as a colorless oil. $^1$H NMR δ: 7.33–7.29 (m, 5H), 5.25 9m, 1H), 5.14 (AB q, J=12.2 Hz), 4.47 (m, 1H), 3.23–3.06 (m, 14H), 1.44–1.31 ( br , 40H), 1.29–1.24 (br, 60H), 0.87 (t, J=6.6 Hz, 3H). Mass spec( ESI+) calcd for : 1369, found 1370 (MH$^+$).

Synthesis of N$^2$-[N$^2$,N$^5$-Bis[((1,1-dimethylethoxy)carbonyl]-N$^2$,N$^5$-bis[3-[(1,1-dimethylethoxy)carbonyl]-aminopropyl]-L-ornithyl]-N-N-dioctadecyl-L-glutamine (2-4) was prepared as follows and used without further purification. A solution of N$^2$-[N$^2$,N$^5$-bis(1,1-dimethylethoxy)carbonyl]-N$^2$,N$^5$-bis[3-[(1,1-dimethylethoxy)carbonyl)aminopropyl]-L-ornithyl]-N,N-dioctadecyl-L-glutamine, phenylmethyl ether, compound 2-3, (4.5 g, 3.2 mmol) in 75 mL of ethyl acetate was hydrogenated in presence 10% Pd/C (450 mg) under 55 psi hydrogen in a Parr hydrogenator. After 12 hours the reaction mixture was filtered to remove the catalyst and concentrated to give compound 2-4 as a colorless oil (4.1 g, 97% yield). $^1$H NMR δ: 9.49 (m, 1H), 4.29 (m, 3H), 3.31–3.23 (m, 16H), 1.28 (m, 60H), 0.89 (t, J=6.6 Hz, 6H).

Compound 2-5 was synthesized according to the following procedure. To the acid, compound 2-4 (3.7 g), was added warm dioxane (20 mL). This solution was cooled to room temperature and then was added 7.0 M solution of HCl in dioxane (20 mL). The reaction mixture was then allowed to stir at room temperature for 5 hours. It was then concentrated at reduced pressure to give a white solid which was coevaporated with heptane (4×10 mL) to give compound 2-5 a white solid (quantitative yield). $^1$H NMR (CD$_3$OD) δ: 4.50 (t, J=6.0 Hz, 1H), 4.15 (m, 1H), 3.38–3.11 (m, 14H), 2.59–2.55 (m, 2H), 1,61–1.56 (m, 4H), 1.54 (br, 60H), 0.90 (t J=6.0 Hz, 6H). Mass spec (ESI+) calcd for 879, found 880 (MH+) (ESI–) found: 878.

Example 3

Synthesis of N$^2$-[N$^2$,N$^5$-Bis(aminopropyl)-L-ornithyl]-N-N-dioctadecyl-L-a-glutamine, tetrahydrotrifluoroacetate (3-5)

Synthesis of 4-[(1,1-dimethylethoxy)carbonyl]amino-5-(dioctadecyl)amino-5-oxopentanoic acid, phenylmethylester (3-1) was prepared as follows and used without further purification. To a solution (338 mg, 1.0 mmol) of Boc-Glu-g-benzyl ester in DCM (10 mL) was added dioctadecylamine (574 mg 1.1 mmol), DCC (227 mg, 1.1 mmol) and HOBt (14 mg, 0.1 mmol). The reaction mixture was allowed to stir at room temperature for 3 days and then filtered. The filtrate was concentrated under reduced pressure to give a colorless oil that was purified by silica gel chromatography (4:1 heptanes:ethyl acetate) to afford 717 mg (85% yield) of compound 3-1. $^1$H NMR δ: 7.36–7.29 (m, 5H), 5.39–5.36 (m 1H), 5.13 (AB q, J=12.0 H), 4.66, 4.61 (m, 1H), 3.52–3.45 (m, 2H), 3.09–3.07 (m, 2H), 1.41 (s, 9H), 1.41 (br, 60H), 0.88 (t, J=6.0 Hz, 6H).

Synthesis of 5-(Dioctadecyl)amino-5-oxopentanoic acid, phenylmethyl ester, hydrotrifluoroacetate (3-2) was prepared using standard Boc deprotecting procedures (see, e.g., Example 2 using TFA:DCM (1:1) (quantitative yield). $^1$H NMR δ: 7.56–7.36 (m, 5H), 5.18, (AB q, J=12.2 Hz), 4.35 (br dd, J=4.2, 3.3 Hz. 1H), 3.57 (dd overlapping dd, 2H), 3.22–3.12 (dd over laps dd, 2H), 2.60 (dd over laps dd 2H), 2.07–2.05 9m, 2H), 1.59–1.57(m, 4H), 1.27 9(br s, 60H), 0.88 (t, J=6.3 Hz, 6H).

Synthesis of N$^2$-[N$^2$,N$^5$-bis(1,1-dimethylethoxy)-carbonyl]-N$^2$,N$^5$-bis[3-[(1,1-dimethylethoxy)carbonyl]-aminopropyl]-L-ornithyl]-N,N-dioctadecyl-L-a-glutamine, phenylmethyl ester (3-3) was prepared as follows and used without further purification. (4S)-5-(Dioctadecyl)amino-5- oxopentanoic acid, phenylmethyl ester, hydrotrifluoroacetate (3-2) (285 mg 0.33 mmol) was coupled with compound 1-6 (261 mg, 0.35 mmol) using protocol such as described in Example 1. The crude product was purified by silica gel chromatography gave 200 mg (60% yield) of compound 3-3. (Also recovered was 150 mg of starting amine). $^1$H NMR δ: 7.34–7.29 9m, 5H), 5.10 (br 2H), 3.16–3.10 (m, 14 H), 1.47 (m overlaps singlet, 40 H), 1.24 (m, 60H), 0.87 (t, J=6.3 Hz, 6H).

Synthesis of $N^2$-[$N^2$,$N^5$-Bis[(1,1-dimethylethoxy) carbonyl]-$N^2$,$N^5$-bis[3-[(1,1-dimethylethoxy)carbonyl]-aminopropyl]-L-ornithyl]-N-N-dioctadecyl-L-a-glutamine (3-4) was prepared by catalytic hydrogenation of 3-3 in EtOAc under 55 psi using 10% Pd/C (85% yield) (see Example 2).

Compound 3-5 was synthesized according to the following procedure. Compound 3-4 was subjected to standard Boc deprotection using TFA:DCM (1:1) to give compound 3-5 in quantitative yield (see Example 1). $^1$H NMR (CD$_3$OD/CDCl$_3$) δ: 4.01–3.98 (m, 1H), 3.59–3.57 (m 2H), 3.16–3.01 (m, 12H), 3.01 (m, 2H), 1.21(br m, 60H), 0.89 (t, J=6.6 HZ). Mass spec: calcd 879. found 880 (MH+).

Example 4

Synthesis of $N^2$-[$N^2$,$N^5$-Bis(3-aminopropyl)-L-ornithyl]-N,N-dioctadecyl-L-a-asparagine, tetrahydrotrifluoroacetate (4-5)

Synthesis of 3-Amino-4-(dioctadecyl)amino-4-oxobutanoic acid, phenylmethyl ester (4-1) was prepared as follows and used without further purification. Boc-Asp-b-benzyl ester was coupled with dioctadecylamine using DCC coupling procedures such as those described in Examples 2. (quantitative yield of compound 4-1). $^1$H NMR δ: 7.39–7.27 (m, 5H), 5.28 (br d, J=12 Hz, 1H), 5.10, (AB q, J=12.0 Hz, 2H), 4.94, (dd, J=5.4, 6.0 Hz, 1H), 3.40–3.15 (m, 4H), 2.82 (dd, J=6.0, 15.6 Hz, 1H), 2.63 (dd, J=5.9, 15.6 Hz, 1H), 1.47 (m overlaps s, 13 H), 1.25 (br m, 60H, 0.87 (t, J=6.3 Hz, 6H).

Synthesis of 3-Amino-4-(dioctadecyl)amino-4-oxobutanoic acid, phenylmethyl ester, hydrotrifluoroacetate (4-2) was prepared as follows and used without further purification. (3S)-3-Amino-4-(dioctadecyl)amino-4-oxobutanoic acid, phenylmethyl ester, compound 4-1, was exposed to TFA to remove Boc protecting group. A quantitative yield of compound 4-2 was obtained. $^1$H NMR δ: 7.39 (m, 5H), 5.19 (AB q, J=12.3 Hz, 2H), 4.55 (t, J=6.3, Hz, 1H), 3.54–3.10 (m, 4H), 2.90 (d, J=6.1 Hz, 2H), 1.60–1.50 (m, 4H), 1.38 (m, 60H), 0.89 ( t, J=6.6 Hz, 6H).

Synthesis of $N^2$-[$N^2$,$N^5$-Bis[(1,1-dimethylethoxy) carbonyl]-$N^2$-$N^5$-bis[(1,1-dimethylethoxy)-carbonyl] aminopropyl]-L-ornithyl]-N,N-dioctadecyl-L-a-asparagine, phenylmethyl ester. (4-3) was prepared as follows and used without further purification. 3-Amino-4-(dioctadecyl) amino-4-oxobutanoic acid, phenylmethyl ester, hydrotrifluoroacetate (4-2) (420 mg, 0.5 mmol) was dissolved in dry DCM (5 mL). To this solution was added TEA (1.0 mL); the reaction mixture was allowed to stir for 5 minutes, at which time tetra-Boc-carboxy spermine succinimidyl ester (369 mg, 0.5 mmol) was added in one portion. After 12 hours the reaction mixture was concentrated under reduced pressure and the crude product was purified by silica gel chromatography (7:3 heptanes:EtOAc) to afford 186 mg of product (27% yield).

Synthesis of $N^2$-[$N^2$,$N^5$-Bis[(1,1-dimethylethoxy) carbonyl]-$N^2$-$N^5$-bis[3-[(1,1-dimethyl-ethoxy)carbonyl] aminopropyl]-L-ornithyl]-N-N-dioctadecyl-L-a-asparagine (4-4) was prepared as follows and used without further purification. $N^2$-[$N^2$,$N^5$-Bis[(1,1-dimethylethoxy)carbonyl]-$N^2$-$N^5$-bis[(1,1-dimethylethoxy)-carbonyl]aminopropyl]-L-ornithyl]-N,N-dioctadecyl-L-a-asparagine, phenylmethyl ester (4-3) (186 mg, 0.13 mmol) was hydrogenated using standard procedures (see Example 2) to afford 92 mg of product (53% yield).

Compound 4-5 was synthesized according to the following procedure. $N^2$-[$N^2$,$N^5$-Bis[(1,1 dimethylethoxy) carbonyl]-$N^2$-$N^5$-bis[3-[(1,1-dimethylethoxy)carbonyl] aminopropyl]-L-ornithyl]-N-N-dioctadecyl-L-a-asparagine (4-4) was subjected to standard Boc deprotection conditions (see Example 1). to give the product as a white waxy solid (94% yield). $^1$H NMR δ: 3.84 (t, J+4.5 Hz, 1H), 3.49–3.44 (m, 1H), 3.33–3.26 (m. 2H), 3.07–2.93 (m, 12H), 2.68–2.59 (m, 2H), 2.04–1.68 (m, 12 H), 1.19 (br m, 60H), 0.80 9t J=5.4 Hz). Mass spec calcd: 865 found: 866 (MH+)

Example 5

Synthesis N-[$N^2$-[$N^2$,$N^5$-Bis[(1,1-dimethylethoxy) carbonyl]- $N^2$,$N^5$-bis[3-[(1,1-dimethylethoxy) carbonyl]aminopropyl]-L-ornithyl-N-N-dioctadecyl-L-glutaminyl]-L-glutamic acid (5-6)

Synthesis of $N^2$-(1,1-Dimethylethoxy)carbonyl-N-N-dioctadecyl-L-glutamine (5-1) was prepared as follows and used without further purification. $N^2$-[1,1-Dimethylethoxy) carbonyl]-N,N-dioctadecyl-L-glutamine, phenylmethyl ester (2-1) (2.4 g, 2.85 mmol) was dissolved in 30 mL of ethyl acetate and 500 mg of 10% Pd/C was added to this solution. The resulting mixture was hydrogenated in a Parr hydrogenation apparatus at 55 psi for 12 hours. The catalyst was filtered and the filtrate was concentrated to give the product, compound 5-1, as colorless oil.

Synthesis of N-[$N^2$-(1,1-Dimethylethoxy)carbonyl-N-N-dioctadecyl-L-glutaminyl]-L-glutamic acid, bis (phenylmethyl)ester (5-2) was prepared as follows and used without further purification. $N^2$-(1,1-Dimethylethoxy) carbonyl-N-N-dioctadecyl-L-glutamine 5-1, (680 mg, 0.9 mmol) was coupled with L-glutamic acid, bis (phenylmethyl)ester, toluene sulfonic acid salt (450 mg, 0.9 mmol) using standard DCC, HOBt mediated coupling (see Examples 2 and 3) to afford 812 mg of product (85% yield). $^1$H NMR δ: 7.88 (m, 1H), 7.38–7.32 (m, 10H), 5.83 (br, 1H), 5.17, 5.12 (2 apparent s, 4H), 4.68 (m, 1H), 4.15 (dd, J=4.6, 6 Hz, 1H), 3.30–3.18 (m, 4H), 2.48–2.42 (m, 5H), 2.1–1.09, (m, 4H), 1.55–1.53 (m, 4H), 1.20 (br, 60H), 0.91 (t, J=6.6 Hz).

Synthesis of N-[N,N-Dioctadecyl-L-glutaminyl]-L-glutamic acid, bis(phenylmethyl)ester, hydrotrifluoroacetate (5-3) was prepared as follows and used without further purification. [N-[$N^2$-(1,1-Dimethylethoxy)carbonyl-N-N-dioctadecyl-L-glutaminyl]-L-glutamic acid, bis (phenylmethyl)ester(5-2) was subjected to standard TFA deprotection (see, e.g., Example 2). This product was used in Example 5 with out further characterization.

Synthesis of N-[$N^2$-[$N^2$,$N^5$-Bis[(1,1-dimethylethoxy) carbonyl]-$N^2$-$N^5$-bis[3-[1,1-dimethylethoxy)carbonyl] aminopropyl]-L-ornithyl]-N-N-dioctadecyl]-L-glutaminyl]-L-glutamic acid, bis(phenylmethyl)ester (compound 5-4) was prepared as follows and used without further purification. Compound 5-3 (200 mg, 0.19 mmol) was coupled with $N^2$,$N^5$-Bis[(1,1-dimethylethoxy)carbonyl]-$N^2$,$N^5$-bis[3-[(1,1-dimethylethoxy)carbonyl]aminopropyl]-L-ornithine, N-hydroxysuccinimydyl ester (1-6)(156 mg, 0.21 mmol) in DCM (5 mL). After 6 hours the reaction mixture was concentrated under reduced pressure and the crude product thus obtained was purified by silica gel chromatography (10% MeOH in DCM) to afford 270 mg of product as a white foamy solid. (90% yield) $^1$H NMR δ: 8.71 (m, 1H), 8.32 9m, 1H), 7.35–7.29 (m, 10H), 5.35 (m, 2H), 5.20–5.11 (m, 4H), 4.39–4.37 (q, J 6.1 Hz), 3.36–3.10 (m, 14H), 1.45 (br s, 36H), 1.27 (br, 60H), 0.89 (t, J=6.5 Hz, 6H).

Synthesis of N-[$N^2$-[$N^2$,$N^5$-Bis(3-aminopropyl)-L-ornithyl]-N,N-dioctadecyl-L-glutaminyl]-L-glutamic acid, Tetrahydrotrifluoroacetate (5-5) was prepared as follows and used without further purification. Compound 5-4 (200 mg, 0.12 mmol) was hydrogenated with catalytic Pd/C at 55 psi (95% yield). This compound was carried to next stage with out further characterization and/or isolation.

Compound 5-6 was synthesized according to the following procedure. Compound 5-5 (100 mg) was subjected to standard Boc deprotection using TFA (see Example 1). Obtained was the product as dirty white waxy solid (quantitative yield). $^1$H NMR (CDCl$_3$/CD$_3$OD) δ: 7.36 (d, J=3.0 Hz, 1H), 4.54 (dd, J=4.7, 9.0 Hz, 1H), 4.41 (t, J=7 Hz, 1H), 4.00 (m, 1H), 3.37–3.30 (m, 14H), 1.57 (m, 4H), 1.29 (br m, 60H), 0.88 (t, J=6.6HZ, 6H). Mass spec(ESI±): calcd: 1008, found 1009 (MH+) and 1007 (M–H+)

Example 6

Synthesis of Compound 6-5

Synthesis of compound 6-2 was prepared as follows and used without further purification. To a solution of 6-benzyloxycarbonyl amino caprioc acid, (6-1), (300 mg, 1.1 mmol) in 10 mL of DCM, was added dioctadecylamine (DODA) (590 mg, 1.1 mmol), DCC (233 mg, 1.1 mmol) and N-hydroxysuccinimide ("NHS") (143 mg, 1.1 mmol). The reaction mixture was warmed to enable the starting material to complely dissolve. It was then allowed to stir under argon atmosphere for 2 days; then the precipitated DC urea was filtered off. The filtrate was washed with 1N HCl, and then saturated NaHCO$_3$ solution, dried over MgSO$_4$, filtered and concentrated to afford 620 mg (71% yield) of a viscous oil. $^1$H NMR δ: 7.36–7.30 (m, 5H), 5.43 (m, 2H), 4.84 (br m 1H), 3.49–319, (m, 6H), 2.25 (t, J=7.5 Hz, 1H), 1.67–1.50 (m, 6H), 1.26 (br s, 60H), 0.88 (t, J=6.0 Hz, 6H).

Synthesis of Compound 6-3 was prepared as follows and used without further purification. Compound 6-2 (620 mg, 0.62 mmol) was dissolved in 15 mL of a 2:1 mixture of methanol:DCM and 100 mg 10% Pd/C was added. This mixture was subjected to hydrogenation at 35 psi for 12 hours. The reaction mixture was then filtered to remove the catalyst and concentrated to afford 420 mg of Compound 6-3 as a waxy solid. $^1$H NMR δ: 3.25–3.01 (overlapping m, 6H), 2.28 (t, J=7.2 Hz, 2H), 1.81 (m, 2H), 1.64–1.59 (m, 10H), 1.23 (br s, 60H), 0.83 (t, J=6.6 Hz, 6H).

Synthesis of Compound 6-4 was prepared as follows and used without further purification. To a solution of amine, Compound 6-3, (195 mg, 0.3 mmol) in 5 mL of DCM, was added tetraboc carboxyspermine (220 mg, 0.34 mmol) and HOBt (50 mg, 0.37 mmol). To this solution was then added a solution of DDC (70 mg, 0.34 mmol) in 3 mL of DCM. The reaction mxiture was allowed to stir overnight. After usual DCC coupling workup, a crude mixture was obtained that was then purified by chromatography on silica gel (13 g) with hexane:ethyl acetate (4:6) as eluent to afford 75 mg of product, Compound 6-4, as a glassy solid. $^1$H NMR δ: 4.38 (br, 1H), 3.24–3.11 (m, 16 H), 2.26 (t, J=7.2 H, 2H), 1.57 (overlapping s and m, 50H), 1.24 (br s, 60H), 0.86 (t J=6.6 Hz, 6H). Mass spectometry calculated 1263, observed 1264 (mH+), 1266 (m+Na+).

Compound 6-5 was synthesized according to the following procedsure. Compound 6-4 (4 mg) was subjected to standard Boc deprotecting conditions and workup conditions using trifluoroacetic acid (see Example 1) to give a quantitative yield of the product compound 6-5 as a pale yellow waxy solid. $^1$H NMR δ: 3.3–29 (m, 12 H), 2.4–2.2 (m, 20H), 1.25 (br s, 60H), 0.85 (t, 6H).

Example 7

Preparation and transfection protocols for COS-7, SNB-19, RD and C8161 cells with mixtures of cationic lipids and CAT plasmid A. Culturing and Transfection of Cells Cell lines were plated at 1.5×10$^5$ cells/well in a 12 well plate format on the day before tranfection. Cultures were maintained at 37° C. in 5% CO$_2$. On the next day, when the cells reached approximately 80% confluence, the transfection mixes were prepared as follows: 126 μg of the target CAT plasmid pG1035 (described below) was added to 36.0 mL of Opti-MEM® (Gibco/BRL, Gaithersburg, Md.) to make a plasmid stock solution. 63 μg of each lipid mix (from a high concentration stock in 100% ethanol) was added to individual 1.5 mL aliquots Opti-MEM® and mixed thoroughly. Then, 2 mL of the DNA stock (containing 7 μg of plasmid) were added to each 1.5 mL aliquot of lipid/Opti-MEM® and gently vortexed. This procedure yielded 3.5 mL of plasmid/lipid mixture at 2 μg/mL plasmid and 18 μg/mL lipid for a 9 to 1 lipid to DNA ratio. The quantity of ethanol in the final cell cultures was 2% or less. This small quantity of ethanol was confirmed to have no adverse effect on any of the cell lines.

In order to prepare cells for transfection, the culture medium was then aspirated out of the wells and the cells were rinsed twice in 1 mL Opti-MEM® per well. The transfection experiments were performed in triplicate; thus, 1 mL of each transfection mix was then added to each of three wells. The cells were cultured in the transfection mix for 5 to 6 hours. The transfection mix was then removed and replaced with 1 mL is of complete culture medium (DMEM or DMEM/F12 plus 10% fetal bovine serum and 1:100 dilution of penicillin:streptomycin stock, all from Gibco/BRL, (Gaithersburg, Md.) and the cells were allowed to recover overnight before expression the CAT gene was measured.

Cell lysates were prepared by rinsing twice in PBS and then were treated with 0.5 mL of 1X Reporter Lysis Buffer (Promega, Madison, Wis.). The lysed cells were pipetted into 1.5 mL tubes and frozen in CO$_2$/EtOH once and thawed. The crude lysate was then clarified by microcentrifugation at 14,000 rpm for 10 minutes to pellet cell debris. The clear supernatant was recovered and assayed directly or stored at –20° C. for assay later.

The cell lysates were then assayed for CAT activity and the total protein concentration was determined as described below in Example 7. The CAT activity was normalized to total protein and plotted as shown.

B. Chloramphenicol Acetyltransferase Assay

This assay was performed generally as follows. First, the following reaction mixture was prepared for each sample:

65 mL 0.23 M Tris, pH 8/0.5% BSA (Sigma, St. Louis, Mo.), 4 mL $^{14}$C-chloramphenicol, 50 nCi/mL (Dupont, Boston, Mass.), and 5 mL mg/mL n-butyryl coenzyme A (Pharmacia, Piscataway, N.J.).

A CAT activity standard curve was prepared by serially diluting CAT stock (Promega, Madison, Wis.) 1:1000, 1:10, 000 and 1:90,000 in 0.25 M Tris, pH 8:0.5% BSA. The original stock CAT was at 7000 Units/mL. CAT lysate was then added in a labeled tube with Tris/BSA buffer for final volume of 50 mL.

Approximately 74 mL of reaction mixture was then added to each sample tube, which was then typically incubated for approximately 1 hour in a 37° C. oven. The reaction was terminated by adding 500 mL pristane:mixed xylenes (2:1) (Sigma, St. Louis, Mo.) to each tube. The tubes were then vortexed for 2 minutes and spun for 5 minutes. Approximately 400 mL of the upper phase was transferred to a scintillation vial with 5 mL Scintiverse (Fisher, Pittsburgh, Pa.). The sample was then counted in a scintillation counter (Packard).

C. Preparation of Plasmid pG1035

The plasmid pG1035 was used for transient transfections of COS-7 (ATCC # CRL-1651), SNB-19, C8161 and RD (ATCC # CCL-136) cells. pG1035 consists of a modified CAT (choramphenicol acetyl transferase) gene (named SplicerCAT) inserted into the eukaryotic vector pRc/CMV (Invitrogen, San Diego, Calif.). SplicerCAT was created by inserting an artificial intron into the wild type CAT gene sequence in a plasmid named pG1036 (also based on pRc/CMV) using the polymerase chain reaction. Transfection results are set forth in Tables IA to ID.

(i) Description of inserted CAT sequences of plasmids pG1035 and pG1036. The sequences of the synthetic splice sites of pG035 (SplicerCAT) and pG1036 (wild-type CAT) are set forth below:

(a) Partial sequence of the wild type CAT gene used to create plasmid pG1036:

```
                      +409 +410      [SEQ. ID. NO. 1]
                       |    |
        GCC UAU UUC CCU AUU UCC CUA AAG
        GGU UUA UUG AGA AUA
```

(b) Full sequence of the intron inserted within the CAT coding sequence of pG1036 to create the SplicerCAT gene and plasmid pG1035:

```
                    +409 1                                    [SEQ. ID. NO. 2]
                     |  |
    ... ACC UGG CCU AUU UCC CUA AAG^gug agu gac uaa cua agu 39
                     |
    cga cug cag acu agu cau ug(a) uug agu gua aca aga ccg 87 +410
                     |  |
    gau auc uuc gaa ccu cuc ucu cuc ucu cag^GGU UUA UUG
    AGA...
```

(ii) Preparation of Plasmids

The region of the CAT gene into which the intron was inserted is shown as the mRNA in sequence (a) above. The wild type CAT gene (Pharmacia) was inserted into pRc/CMV (Invitrogen, San Diego, Calif.) via Hind III restriction sites to create plasmid pG1036. Bases +409 and +410 are labeled on SEQ. ID. NOS. 1 and 2 for comparison of sequences only to pG1035. A synthetic intron, shown in sequence (b) above, was inserted into the CAT DNA to create plasmid pG1035. Mature mRNA sequences are shown uppercase, intronic sequences are lower case. The canonical guanosine of the splice donor is labeled +409, which corresponds to base +409 of the CAT open reading frame. The first base of the intron is labeled 1. The canonical branchpoint adenosine is base 39 and the canonical intronic splice acceptor guanosine is base 87 of the intron. Base +410 marks the resumption of the CAT open reading frame. The sequences against which the oligomers are targeted are underlined. The consensus splice site bases are given in bold face italics (Smith et al., *Ann. Rev. Genet.* 23: 527, 1989; and Green, *Ann. Rev. Genet.* 20: 671, 1986).

The clone pG1035 was assembled from two fragments created using phosphorylated synthetic DNA PCR primers and plasmid pG1036 as the PCR template in two separate PCR reactions. One reaction produced a Hind III-Spe I 5'-fragment containing the first ⅔ of the open reading frame and half of the synthetic intron. The second PCR reaction produced an Spe I-Not I fragment containing the second half of the intron and the last ⅓ of the open reading frame. These PCR products were combined with Hind III-Not I cut pRc/CMV in a 3-way ligation to yield the final plasmid. The artificial CAT gene containing the intron is named Splicer-CAT. References applicable to the foregoing include Smith et al., supra and Green supra.

D. Coomassie Protein Assay

The total protein content of the clarified cell lysates was determined by mixing 6 μL of each cell lysate to 300 mL of Coomassie protein assay reagent (Pierce, Rockford, Md.) in the wells of an untreated microtiter assay plate. Concentration curve standards were prepared using 6 μL of 0, 75, 100, 200, 250, 400, 500, 1000, and 1500 mg/mL BSA stock solutions and 300 mL of the Coomassie reagent. The assay samples were allowed to sit for approximately 30 minutes before reading the optical absorbance at 570 nm in a microplate reader (Molecular Probes).

The cells were assayed for CAT protein as described above. The results of the transfection efficiency of the cationic lipids are tabulated in Tables IA to ID.

Example 8

FITC-Oligonucleotide Uptake Assay

A. Oligomers Used

The oligonucleotides used for the determination of cationic lipid mediated oligonucleotide uptake in all cell lines tested were:

3498-PS: 5' FITC-ggt-ata-tcc-agt-gat-ctt-ctt-ctc [SEQ. ID NO. 1],

Oligomer 3498-PS has an all-phosphorothioate backbone. This oligonucleotide has 23 negative charges on the backbone and is considered to be 100% negatively charged.

3498: 5' FITC-ggt-ata-tcc-agt-gat-ctt-ctt-ctc [SEQ. ID NO. 2],

Oligomer 3498 is a chimeric oligonucleoside. The underlined bases were linked by a phosphorothioate backbone, while the other linkages in the oligomer consisted of alternating methylphosphonates and phosphodiesters. The oligomer had 11 methylponate, 7 diester, and 5 phosphorothioates linkages. The total charge density was 57% of 3498-PS.

3793-2: 5' FITC-ggu-aua-ucc-agu-gau-cuu-cut [SEQ. ID NO. 3],

Oligomer 3293-2 has an alternating methylphosphonate and diester backbone with all 2'-O-methyl groups on each ribose in the oligonucleotide. The total charge density was 50% of 3498-PS.

Stocks of oligomers 3498-PS and 3498 were prepared at 300 micromolar, while the oligomer 3793–2 stock was prepared at 440 micromolar B. Reagents and Cells The commercially available lipids used in the assays were:

Lipofectin® ("LFN") Lot#EF3101 1 mg/mL, Gibco/BRL (Gaithersburg, Md.)
LipofectAMINE® ("LFA") Lot#EFN101 2 mg/mL, Gibco/BRL (Gaithersburg, Md.)
Transfectam® ("TFM") Lot#437121 1 mg dry, Promega, (Madison, Wis.) and resuspended in 100% ethanol.

The novel lipids of the present invention used in these evaluations, as listed in the data tables (Tables II A to C), were at 1 mg/mL in 100% ethanol.

The tissue culture cell stocks, SNB-19 (human glioblastoma), C8161 (a human amelanotic melanoma), RD (human rhabdomyosarcoma, ATCC # CCL-136) and COS-7 (African green monkey kidney cells, ATCC # CRL-1651) were maintained in standard cell culture media: DMEM:F12 (1:1) mix from Mediatech, Lot#150901126, 10% fetal bovine serum from Gemini Bioproducts, Lot#A1089K, 100 units/mL penicillin and 100 micrograms/mL streptomycin, from Mediatech, Lot#30001044 and 365 micrograms/mL L-glutamine. The cells were maintained under standard conditions (37° C., 5% $CO_2$ atmosphere) at all times prior to fixation and microscopic examination.

C. Preparation of Cells and Transfection Mixes

For each FITC labeled oligomer delivery determination, the appropriate cells were plated into 16 well slides (Nunc #178599, glass microscope slide with 16 removable plastic wells attached to the slide surface with a silicone gasket) according to standard tissue culture methods. Each cell line was plated at a starting density (approximately 20,000 cells/well) that allowed them to be healthy and 60–80% confluent one to two days after plating. The cells to were allowed to adhere to the glass and recover from the plating procedure in normal growth medium for 24 to 48 hours before beginning the transfection procedure.

Oligonucleotide transfection mixes were made up in Opti-MEM® without antibiotics as follows: 500 μL aliquots of Opti-MEM® containing a 0.25 micromolar solution of either oligomer 3498-PS, 3498, or 3793-2 (2 micrograms of oligomer per sample) were pipetted into 1.5 mL Eppendorf tubes. Cationic lipid or lipid mixture was then added to the oligomer solution to give a final 9:1 or 6:1 ratio (18 or 12 μg of lipid total) of cationic lipid to oligomer by weight, as listed in Tables IIA to IIC. The tubes were mixed by vortexing immediately after the addition of lipid.

Prior to beginning the transfection reactions the cells were rinsed in 200 μL Opti-MEM®; then, the cells were rinsed with Dulbecco's phosphate buffered saline (PBS) solution, and 200 μL of oligomer transfection mix was added directly to a well to begin each transfection reaction. Transfection reactions were allowed to continue for four to six hours.

At that time, the cells were then rinsed in PBS from Mediatech and fixed for ten minutes in 200 μL of 3.7% formaldehyde (Sigma, St. Louis, Mo.) to terminate the transfection reaction. Then the wells were rinsed again in PBS. The formaldehyde was quenched with 200 μL of 50 mM glycine (Sigma, St. Louis, Mo.) for ten minutes. Finally, the wells were then emptied by shaking out the glycine solution. At that time, the plastic chambers and silicone gasket were removed and the cells were covered with Fluoromount-G mounting medium (from Fisher, Pittsburgh, Pa., with photobleaching inhibitors) and a cover slip.

Intracellular fluorescence was evaluated under 200× magnification with a Nikon Labophot-2 microscope with an episcopic-fluorescence attachment. Using this equipment we could distinguish extracellular from nuclear and endosomal fluorescence.

The cells were scored for uptake of FITC labelled oligomer as follows: No nuclear fluorescence, 0; up to 20% fluorescent nuclei, 1; up to 40% fluorescent nuclei, 2; up to 60% fluorescent nuclei, 3; up to 80% fluorescent nuclei, 4; and up to 100% fluorescent nuclei, 5.

The results of the transfections in COS-7, SB-19, C-8161 and RD cells are tabulated in Tables IIA to IIC.

TABLE I

Transient transfection efficiency of cationic lipids in COS-7, SNB-19, RD and C8161 cells

| Lipid | Mean | SDV | REL |
|---|---|---|---|
| A. Cell line COS-7 | | | |
| None | 894 | 23 | 0 |
| Transfectam | 89437 | 14746 | 0.52 |
| Lipofectamine | 119902 | 7350 | 0.7 |
| Lipofectin | 57084 | 4288 | 0.33 |
| 2-5 | 55598 | 4643 | 0.33 |
| 2-5/DOPE | 159419 | 18564 | 0.93 |
| 2-5/7-1 | 162560 | 9944 | 0.95 |
| 1-9/DOPE | 170801 | 5457 | 1 |
| 1-10 | 148040 | 3932 | 0.87 |
| 1-10/DOPE | 138397 | 11512 | 0.81 |
| B. Cell line SNB-19 | | | |
| None | 807 | 24 | 0 |
| Transfectam | 106060 | 17596 | 0.56 |
| Lipofectamine | 143064 | 12699 | 0.76 |
| Lipofectin | 177312 | 3487 | 0.94 |
| 2-5 | 103280 | 12908 | 0.55 |
| 2-5/DOPE | 134725 | 13224 | 0.71 |
| 2-5/7-1 | 172245 | 99236 | 0.91 |
| 1-9/DOPE | 187651 | 5480 | 1 |
| 1-10 | 166179 | 18702 | 0.88 |
| 1-10/DOPE | 188468 | 2650 | 1 |
| C. Cell line RD | | | |
| None | 743 | 32 | 0 |
| Transfectam | 51255 | 1490 | 0.29 |
| Lipofectamine | 85689 | 9618 | 0.48 |
| Lipofectin | 128481 | 8972 | 0.72 |
| 2-5 | 73921 | 3839 | 0.41 |
| 2-5/DOPE | 104283 | 6701 | 0.58 |
| 2-5/7-1 | 178331 | 4630 | 1 |
| 1-9/DOPE | 123060 | 5312 | 0.69 |
| 1-10 | 124232 | 5248 | 0.7 |
| 1-10/DOPE | 42824 | 2629 | 0.24 |
| D. Cell line C8161 | | | |
| None | 851 | 32 | 0 |
| Transfectam | 141138 | 2049 | 0.71 |
| Lipofectamine | 133571 | 5823 | 0.67 |
| Lipofectin | 144780 | 11981 | 0.73 |
| 2-5 | 137710 | 16610 | 0.69 |
| 2-5/DOPE | 199253 | 5307 | 1 |
| 2-5/7-1 | 153079 | 13322 | 0.77 |
| 1-9/DOPE | 61088 | 8087 | 0.31 |
| 1-10 | 159578 | 6067 | 0.8 |
| 1-10/DOPE | 84229 | 7287 | 0.42 |

TABLE II

Demonstration of nuclear delivery of oligonucleotides of varing charge densities by novel cationic lipids

| Lipids: | Cell lines: | | | |
|---|---|---|---|---|
| | COS7 | SNB19 | C8161 | RD |
| A. 3498-PS (phosphorothioate) | | | | |
| TFM | 4 | 3 | 5 | 4 |
| LFA | 4 | 3 | 4 | 4 |
| LFN | 5 | 3 | 3 | 4 |
| 2-5 | 2 | 3 | 3 | 3 |
| 2-5/DOPE | 4 | 3 | 2 | 3 |
| 2-5/7-1 | 4 | 3 | 2 | 4 |
| 1-9/DOPE | 5 | 3 | 2 | 3 |
| 1-10 | 4 | 4 | 5 | 5 |
| 1-10/DOPE | 5 | 4 | 3 | 3 |
| B. 3498 Chimera | | | | |
| TFM | 5 | 5 | 5 | 5 |
| LFA | 5 | 4 | 5 | 5 |
| LFN | 1 | 2 | 3 | 3 |
| 2-5 | 2 | 3 | 4 | 4 |
| 2-5/DOPE | 4 | 2 | 3 | 3 |
| 2-5/7-1 | 4 | 2 | 4 | 4 |
| 1-9/DOPE | 5 | 3 | 2 | 3 |
| 1-10 | 3 | 4 | 3 | 4 |
| 1-10/DOPE | 3 | 3 | 0 | 1 |
| C. 3793-2 alternating | | | | |
| TFM | 5 | 5 | 5 | 5 |
| LFA | 5 | 4 | 5 | 5 |
| LFN | 0 | 0 | 2 | 0 |
| 2-5 | 1 | 3 | 3 | 4 |
| 2-5/DOPE | 3 | 1 | 1 | 2 |
| 2-5/7-1 | 4 | 3 | 3 | 4 |
| 1-9/DOPE | 4 | 2 | 1 | 0 |
| 1-10 | 0 | 0 | 0 | 0 |
| 1-10/DOPE | 0 | 0 | 0 | 0 |

We claim:

1. A lipid having the structure:

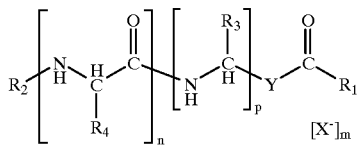

or a salt, or solvate, or enantiomer thereof wherein; (a) Y is a direct link or an alkylene of 1 to about 20 carbon atoms; (b) $R_1$ is H; (c) $R_2$, $R_3$ and $R_4$ are positively charged moieties, or at least one but not all of $R_2$, $R_3$ or $R_4$ is a positive moiety and the remaining are independently selected from H, and alkyl moiety of 1 to about 6 carbon atoms, or a heterocyclic moiety of about 5 to about 10 carbon atoms; (d) n and p are independently selected integers from 0 to 8, such that the sum of n and p is from 1 to 16; (e) $X^-$ is an anion or polyanion and (f) m is an integer from 0 to a number equivalent to the positive charge(s) present on the lipid; provided that if Y is a direct link and the sum of n and p is 1 then one of either $R_3$ or $R_4$ must have an alkyl moiety of at least 10 carbon atoms.

2. A lipid according to claim 1 wherein at least one but not all of $R_2$, $R_3$, and $R_4$ are independently selected from the group consisting of a substituted heterocyclic moiety of 1 to about 6 carbon atoms, or a substituted alkyl moiety of 1 to about 6 carbon atoms substituted with substituents selected from the group consisting of OH, thio, aryl of 1 to about 20 carbon atoms, and $OR_7$, wherein $R_7$ is an alkyl moiety of 1 to about 24 carbon atoms, an alkenyl of 2 to about 24 carbon atoms, an aryl of about 5 to about 20 carbon atoms or an aralkyl of about 6 to about 25 carbon atoms.

3. A lipid according to claim 1 wherein at least one but not all $R_2$, $R_3$, and $R_4$ are independently selected from a group consisting of an alkylamine moiety, a fluoroalkylamine moiety, or a perfluoroalkylamine moiety of 1 to about 6 carbon atoms, an arylamine moiety or an aralkylamine moiety of 5 to about 10 carbon atoms, a guanidinium moiety, an enamine moiety, a cyclic amine moiety, an amidine moiety, an isothiourea moiety, a heterocyclic amine moiety, and a substituted heterocyclic moiety and a substituted alkyl moiety of 1 to about 6 carbon atoms substituted with a substituent selected from the group consisting of $NH_2$, $C(=O)NH_2NHR_7$, $C(=O)NHR_7$, $NHR_7R_8$, and $C(=O)NHR_7R_8$, wherein $R_7$ and $R_8$ are independently selected from an alkyl moiety of 1 to about 24 carbon atoms, an alkenyl moiety of 2 to about 24 carbon atoms, an aryl moiety of about 5 to about 20 carbon atoms, and an aralkyl moiety of about 6 to about 25 carbon atoms.

4. A lipid according to claim 3 herein the arylamine moiety is selected from the group consisting of tryptophane, phenylanaline, and tyrosine.

5. A lipid according to claim 1 wherein $R_2$ is an amino acid residue having a positively charged side chain, and wherein the amino group(s) is optionally substituted with an alkyl of 1 to about 6 carbon atoms or wherein the amino group(s) is substituted to form a secondary, tertiary, or quaternary amine with an alkyl moiety of 1 to about 6 carbon atoms optionally substituted with a group selected from; hydroxyl, amino, alkoxy of 1 to about 6 carbon atoms, alkylamino of 1 to about 6 carbon atoms, or dialkylamino of 2 to about 12 carbon atoms.

6. A lipid according to claim 5 herein $R_2$ is an amino acid residue selected from the group consisting of lysine, arginine, histidine, ornithine, and an amino acid analog.

7. A lipid according to claim 6 wherein the amino acid analog is selected form the group consisting of 3-carboxyspermidine, 5-carboxyspermidine, 6-carboxyspermine and monoalkyl, dialkyl or peralkyl substituted derivatives which are substituted on one or more amine nitrogens with an alkyl group of 1 to about 6 carbon atoms.

8. A lipid according to claim 1 wherein $R_3$ and $R_4$ are independently a lipophilic moiety of 1 to about 24 carbon atoms, a positively charged moiety, or a negatively charged moiety.

9. A lipid according to claim 8 wherein the lipophilic moiety is selected from the group consisting of a straight chain alkyl moiety of 1 to about 24 carbon atoms, a straight chain alkenyl moiety of 2 to about 24 carbon atoms, a symmetrical branched alkyl or alkenyl moiety of about 10 to about 50 carbon atoms, a unsymmetrical branched alkyl or alkenyl moiety of about 10 to about 50 carbon atoms, aryl moiety of about 5 to about 20 carbon atoms, an aralkyl moiety of about 6 to about 25 carbon atoms, and a steroidyl moiety.

10. A lipid according to claim 8 wherein positively charged moiety is selected from the group consisting of amino acid residues having a positively charged group on the side chain, an alkylaminoalkyl moiety, a fluoroalkylaminoalkyl moiety, a perfluoroalkylaminoalkyl moiety, a guanidiniumalkyl moiety, an enaminoalkyl moiety, a cyclic aminoalkyl moiety, an amidinoalkyl moiety, an isothiourea alkyl moiety, and a heterocyclic amine moiety.

11. A lipid according to claim 8 wherein the negatively charged moiety is selected from the group consisting of a carboxyalkyl moiety, a phosphonoalkyl moiety, a sulfonoalkyl moiety, and a phosphatidylalkyl moiety of 1 to about 24 carbon atoms.

12. A lipid according to claim 1 wherein the sum of n and p is from 1 to 8.

13. A lipid according to claim 1 wherein the sum of n and p is from 1 to 4.

14. A lipid according to claim 1 wherein the sum of n and p is from 1 to 2.

15. A lipid according to claim 1 wherein $X^-$ is a pharmaceutically acceptable anion or polyanion.

* * * * *